(12) United States Patent
Sode et al.

(10) Patent No.: US 11,525,121 B2
(45) Date of Patent: Dec. 13, 2022

(54) MUTANT GLUCOSE OXIDASE AND USE THEREOF

(71) Applicant: ARKRAY, Inc., Kyoto (JP)

(72) Inventors: Koji Sode, Tokyo (JP); Kazushige Mori, Tokyo (JP); Katsuhiro Kojima, Tokyo (JP)

(73) Assignee: ARKRAY, INC., Kyoto (JP)

( * ) Notice: Subject to any disclaimer, the term of this patent is extended or adjusted under 35 U.S.C. 154(b) by 0 days.

(21) Appl. No.: 17/034,364

(22) Filed: Sep. 28, 2020

(65) Prior Publication Data
US 2021/0009967 A1 Jan. 14, 2021

Related U.S. Application Data

(62) Division of application No. 16/418,090, filed on May 21, 2019, now Pat. No. 10,822,592.

(30) Foreign Application Priority Data

May 22, 2018 (JP) .............................. JP2018-098011

(51) Int. Cl.
| | | |
|---|---|---|
| *C12N 9/04* | (2006.01) | |
| *C12N 9/96* | (2006.01) | |
| *C12Q 1/00* | (2006.01) | |
| *G01N 27/327* | (2006.01) | |

(52) U.S. Cl.
CPC ............. *C12N 9/0006* (2013.01); *C12N 9/96* (2013.01); *C12Q 1/006* (2013.01); *C12Y 101/03004* (2013.01); *G01N 27/3271* (2013.01)

(58) Field of Classification Search
None
See application file for complete search history.

(56) References Cited

FOREIGN PATENT DOCUMENTS

| JP | 2016-122519 A | 7/2016 |
|---|---|---|
| WO | 2018/062542 A1 | 4/2018 |

OTHER PUBLICATIONS

Yoshikuni et al. Curr Opin Chem Biol. Apr. 2007;11(2):233-9. (Year: 2007).*
Accession A0A1V6NYT5. Jun. 7, 2017. (Year: 2017).*
Accession A0A1V6NX26. Jun. 7, 2017. (Year: 2017).*
Accession B8N4U5. Mar. 3, 2009 (Year: 2009).*
Accession P81156. Jul. 15, 1998 (Year: 1998).*
Accession A0A0L1J5F4. Nov. 11, 2015 (Year: 2015).*
Accession A0A0A2W8T2. Feb. 4, 2015. (Year: 2015).*
Accession B6HFB4. Dec. 16, 2008 (Year: 2008).*
Chua et al., "Plasma Glucose Measurement with the Yellow Springs Glucose Analyzer," Clinical Chemistry, 24: 150-152 (1978).
Pickup et al., "Potentially-Implantable, Amperometric Glucose Sensors with Mediated Electron Transfer: Improving the Operating Stability," Biosensors, 4: 109-119 (1989).
Pakapongpan et al., "Self-assembly of glucose oxidase on reduced graphene oxide-magnetic nanoparticles nanocomposite-based direct electrochemistry for reagentless glucose biosensor," Materials Science & Engineering C, 76: 398-405 (2017).
Hatada et al., "Development of a glucose sensor employing quick and easy modification method with mediator for altering electron acceptor preference," Bioelectrochemistry, 121: 185-190 (2018).
Extended European Search Report issued in corresponding European Patent Application No. 19175806.9 dated Jul. 30, 2019.
Database UniProt [Online], "SubName: Full=Glucose oxidase {ECO:0000313/EMBL:ODM18347.1}," XP002792802, retrieved from EBI accession No. UNIPROT: A0A1E3BBK7, Database accession No. A0A1E3BBK7 (2017).
Ge et al., "Comparative genomic and transcriptomic analyses of the Fuzhuan brick tea-fermentation fungus *Aspergillus cristatus*," BMC Genomics, 17 (428): 1-13 (2016).
Accession B2CNX9 (2008).
Liu et al., "Amperometric glucose biosensor with high sensitivity based on self-assembled Prussian Blue modified electrode," Electrochimica Acta, 54: 7490-7494 (2009).
Yoshikuni et al., "Pathway engineering by designed divergent evolution," Current Opinion in Chemical Biology, 11 (2): 233-239 (2007).

* cited by examiner

*Primary Examiner* — Christian L Fronda
(74) *Attorney, Agent, or Firm* — Morgan, Lewis & Bockius LLP

(57) ABSTRACT

By using a mutant glucose oxidase comprising an amino acid sequence in which a residue corresponding to isoleucine at position 489 or arginine at position 335 in the amino acid sequence of SEQ ID NO:1 is substituted with an amino acid residue having a reactive functional group in a side chain, and binding an electron acceptor to the mutant glucose oxidase through the amino acid residue having a reactive functional group, an electron acceptor-modified glucose oxidase is obtained.

16 Claims, 3 Drawing Sheets

Specification includes a Sequence Listing.

SEQUENCE LISTING

```
<160> NUMBER OF SEQ ID NOS: 11

<210> SEQ ID NO 1
<211> LENGTH: 583
<212> TYPE: PRT
<213> ORGANISM: Aspergillus niger

<400> SEQUENCE: 1

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Thr Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80
```

```
Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
            130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
            210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
            290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495
```

```
Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
                580

<210> SEQ ID NO 2
<211> LENGTH: 606
<212> TYPE: PRT
<213> ORGANISM: Penicillium polonicum

<400> SEQUENCE: 2

Met Lys Leu Leu Gly Val Leu Ser Gly Leu Gly Leu Val Val Ala
1               5                   10                  15

Thr Ala Leu Pro Leu Gln Glu Phe Asp Leu Gln Ser Ser Leu Leu Thr
                20                  25                  30

Asp Pro Arg Lys Val Ala Gly Glu Thr Phe Asp Tyr Val Ile Ala Gly
            35                  40                  45

Gly Gly Leu Thr Gly Leu Thr Val Ala Ala Arg Leu Thr Glu Asn Pro
        50                  55                  60

Asp Ile Asn Val Leu Val Ile Glu Ser Gly Phe Tyr Glu Ser Asn Ile
65                  70                  75                  80

Gly Pro Ile Ile Glu Asn Leu Asn His Tyr Gly Asp Ile Phe Thr Thr
                85                  90                  95

Ser Val Asp Gln Ala Phe Glu Thr Val Pro Leu Ala Ile His Asn Arg
                100                 105                 110

Thr Glu Ile Val Arg Ser Gly Lys Gly Leu Gly Gly Ser Thr Leu Val
            115                 120                 125

Asn Gly Gly Ser Trp Thr Arg Pro His Lys Ala Gln Val Asn Ser Trp
        130                 135                 140

Glu Lys Val Phe Gly Met Glu Gly Trp Asn Trp Asp Asn Leu Leu Pro
145                 150                 155                 160

Tyr Met Asn Lys Val Glu Ala Ser Arg Pro Pro Asn Ala Ala Gln Ile
                165                 170                 175

Ala Ala Gly His Tyr Phe Asp Pro Ala Cys His Gly Val Asn Gly Thr
            180                 185                 190

Val Gln Val Gly Pro Arg Asp Thr Gly Glu Ser Tyr Ser Pro Met Ile
        195                 200                 205

Lys Ser Leu Met Glu Thr Ala Lys Asn Ser Gly Val Pro Val Gln Lys
    210                 215                 220

Asp Phe Ser Cys Gly Val Pro His Gly Ile Ser Met Phe Pro Asn Asp
225                 230                 235                 240

Val His Glu Asp Gln Thr Arg Ser Asp Ala Ala Arg Glu Trp Leu Leu
                245                 250                 255

Pro Asn Tyr Lys Arg Lys Asn Leu Lys Val Leu Thr Gly Gln Met Val
            260                 265                 270

Gly Arg Val Leu Phe Asp Thr Thr Thr Ser Thr Pro Lys Ala Val Gly
        275                 280                 285
```

-continued

Val Asn Phe Gly Thr His Asn Lys Val Asn Phe Asp Val His Ala Lys
290                 295                 300

His Glu Val Leu Leu Ala Ala Gly Ser Thr Val Ser Pro Gln Ile Leu
305                 310                 315                 320

Glu His Ser Gly Val Gly Leu Lys Thr Val Leu Asp Lys Val Gly Val
                325                 330                 335

Lys Gln Leu Val Glu Leu Pro Val Gly Leu Asn Leu Gln Asp Gln Thr
            340                 345                 350

Thr Thr Thr Val Arg Ser Ala Ile Asn Pro Ile Gly Ala Gly Gln Gly
        355                 360                 365

Gln Ala Ala Tyr Phe Ala Thr Phe Asn Glu Thr Phe Gly Asp Gln Ala
370                 375                 380

Pro Arg Ala His Glu Leu Leu Asn Thr Lys Leu Glu Gln Trp Ala Lys
385                 390                 395                 400

Asp Ala Val Ser Arg Gly Gly Phe His Asn Glu Thr Ala Leu Leu Ile
                405                 410                 415

Gln Tyr Glu Asn Tyr Arg Asp Trp Leu Val Asn Ser Asp Val Ser Tyr
            420                 425                 430

Ala Glu Ile Phe Ile Asp Thr Ala Gly Lys Leu Ser Leu Asp Leu Trp
        435                 440                 445

Asp Leu Ile Pro Phe Thr Arg Gly Tyr Val His Ile Leu Asp Ser Asp
450                 455                 460

Pro Tyr Leu Arg Arg Phe Ala Tyr Asp Pro Gln Tyr Phe Leu Asn Glu
465                 470                 475                 480

Leu Asp Leu Leu Gly Gln Ala Ala Ser Lys Leu Ala Arg Glu Ile
                485                 490                 495

Ser Asn Lys Gly Glu Met Thr Lys Tyr Phe Asn Ser Glu Thr Val Pro
            500                 505                 510

Gly Asn Asn Leu Ala Tyr Asp Ala Thr Leu Asp Gln Trp Val Asp Tyr
        515                 520                 525

Val Lys Gln Asn Phe Arg Pro Asn Tyr His Gly Val Gly Thr Cys Ser
530                 535                 540

Met Met Ser Lys Glu Leu Gly Gly Val Val Asp Ala Ala Ala Arg Val
545                 550                 555                 560

Tyr Asp Val Glu Gly Leu Arg Val Ile Asp Gly Ser Ile Pro Pro Thr
                565                 570                 575

Gln Val Ser Ser His Val Met Thr Val Phe Tyr Gly Met Ala Glu Lys
            580                 585                 590

Ile Ser Glu Ala Ile Leu Ala Asp Tyr His Ala Ala Ser Asn
        595                 600                 605

<210> SEQ ID NO 3
<211> LENGTH: 614
<212> TYPE: PRT
<213> ORGANISM: Penicillium polonicum

<400> SEQUENCE: 3

Met Lys Ser Ile Ile Phe Ser Cys Phe Leu Ile Ser Val Ala Ala Ser
1               5                   10                  15

Lys Arg Tyr Leu Pro Ser Glu Gln Ile Asp Val Gln Ser Ser Leu Leu
            20                  25                  30

Ser Asp Pro Thr Gln Val Thr Gly Lys Thr Val Asp Tyr Ile Ile Ala
        35                  40                  45

Gly Gly Gly Leu Thr Gly Leu Thr Ile Ala Ala Lys Leu Thr Glu Asp
    50                  55                  60

```
Pro Ser Ile Glu Val Leu Val Ile Glu Asn Gly Phe Tyr Glu Ser Thr
 65                  70                  75                  80

Asp Gly Asp Ile Ile Glu Asp Leu Asn Asp Tyr Gly Asp Ile Phe Gly
             85                  90                  95

Thr Thr Val Asp His Ala Tyr Glu Ile Val Pro His Pro Ile Asn Asn
            100                 105                 110

Arg Thr Glu Asn Val Arg Ser Gly Asn Gly Leu Gly Gly Ser Thr Leu
        115                 120                 125

Ile Asn Gly Gly Ser Trp Thr Arg Pro His Lys Ala Gln Ile Asp Ser
    130                 135                 140

Trp Glu Lys Val Phe Gly Asn Lys Gly Trp Asn Trp Asp Asp Met Leu
145                 150                 155                 160

Pro Tyr Met Gln Lys Val Glu Ile Ser Arg Pro Pro Ser Asp Val Glu
                165                 170                 175

Ile Ala Ala Gly His Tyr Tyr Asn Ser Thr Cys His Gly Thr Asn Gly
            180                 185                 190

Thr Val His Ala Gly Pro Arg Asn Asn Gly Glu Pro Tyr Ser Pro Ile
        195                 200                 205

Ile Lys Ala Leu Met Asp Thr Ala Lys Gly Arg Gly Val Pro Thr Gln
    210                 215                 220

Leu Asp Phe His Cys Gly Val Pro Arg Gly Val Ser Met Ile Pro Asn
225                 230                 235                 240

Gly Leu His Glu Asp Gln Ile Arg Ser Asp Ala Ala Arg Glu Trp Leu
                245                 250                 255

Leu Pro Asn Tyr Lys Arg Pro Asn Leu Gln Val Leu Thr Gly Gln Phe
            260                 265                 270

Val Gly Lys Val Leu Ile Asn Gln Thr Thr Ser Gly Ala Val Ser
        275                 280                 285

Gly His Lys Ala Val Gly Val Asn Phe Gly Thr Asn Lys Asn Val Asn
    290                 295                 300

Phe Asn Val Tyr Ala Lys His Glu Val Leu Leu Ala Ser Gly Ser Val
305                 310                 315                 320

Val Ser Pro Arg Ile Leu Glu Tyr Ser Gly Ile Gly Leu Lys Ser Val
                325                 330                 335

Leu Asp Thr Ala Gly Ile Gln Gln Ile Val Asp Leu Pro Val Gly Leu
            340                 345                 350

Asn Met Gln Asp Gln Thr Thr Thr Val Ala Ser Arg Ile Lys Ser
        355                 360                 365

Ser Gly Asn Gly Gln Gly Gln Ala Ile Tyr Phe Ala Thr Phe Asn Glu
    370                 375                 380

Thr Phe Gly Asp Tyr Ala Pro Gln Ala His Lys Leu Leu Asn Thr Lys
385                 390                 395                 400

Leu His Gln Trp Ala Thr Glu Thr Val Ala Arg Gly Gly Phe His Asn
                405                 410                 415

Val Thr Ala Leu Glu Ile Gln Tyr Gln Asn Tyr Arg Asp Trp Leu Val
            420                 425                 430

Asn Glu Glu Val Ala Tyr Thr Glu Leu Phe Leu Asp Thr Ser Gly Lys
        435                 440                 445

Ile Asn Phe Asp Leu Trp Asp Leu Ile Pro Phe Thr Arg Gly Ser Val
    450                 455                 460

His Ile Glu Gly Asn Asp Pro Tyr Leu Arg Arg Phe Ser Tyr Asp Pro
465                 470                 475                 480
```

```
Lys Phe Phe Met Asn Asp Leu Asp Leu Leu Gly Gln Ala Ala Gly Ser
            485                 490                 495

Lys Leu Ala Arg Glu Ile Ser Asn Ser Gly Asp Met Gln Thr Tyr Phe
            500                 505                 510

Asp Gly Glu Thr Thr Pro Gly Asp Asn Leu Glu Tyr Asp Ala Asp Leu
            515                 520                 525

Asp Gln Trp Val Asp Tyr Val Lys Gln Asn Phe Arg Ala Asn Trp His
        530                 535                 540

Ala Val Gly Thr Cys Ser Met Met Ala Lys Glu Leu Gly Gly Val Val
545                 550                 555                 560

Asp Ser Glu Ala Arg Val Tyr Gly Val Glu Gly Leu Arg Val Val Asp
            565                 570                 575

Gly Ser Ile Pro Pro Thr Gln Val Ser Ser His Val Met Thr Ile Phe
            580                 585                 590

Tyr Ala Met Ala Leu Lys Ile Ser Asp Ala Val Leu Thr Asp Phe His
            595                 600                 605

Ala Lys Ser Ser Lys Asn
        610

<210> SEQ ID NO 4
<211> LENGTH: 605
<212> TYPE: PRT
<213> ORGANISM: Aspergillus flavus NRRL3357

<400> SEQUENCE: 4

Met Lys Ser Ala Ile Phe Ser Pro Ile Leu Phe Ser Leu Ala Leu Ala
1               5                   10                  15

Gln Asn Tyr Ser Leu Glu Lys His Phe Asp Val Gln Ser Ser Leu Ile
            20                  25                  30

Ser Asp Pro Lys Glu Val Ser Glu Lys Thr Phe Asp Tyr Val Ile Ala
        35                  40                  45

Gly Gly Gly Leu Thr Gly Leu Thr Val Ala Thr Lys Leu Thr Glu Asn
    50                  55                  60

Pro Asp Ile Glu Val Leu Val Ile Glu Lys Gly Phe Tyr Glu Ser Asn
65                  70                  75                  80

Cys Gly Ser Ile Val Glu Asp Leu Asn Glu Tyr Gly Asp Ile Phe Gly
                85                  90                  95

Thr Asp Val Asp Gln Ala Tyr Gln Thr Val Pro Leu Ala Val Asn Asn
            100                 105                 110

Arg Thr Glu Leu Ile Arg Ser Gly Asn Gly Leu Gly Gly Ser Thr Leu
        115                 120                 125

Ile Asn Gly Gly Ser Trp Thr Arg Pro Asp Lys Val Gln Ile Asp Ser
    130                 135                 140

Trp Glu Arg Val Phe Gly Asn Glu Gly Trp Asn Trp Asp Ser Leu Phe
145                 150                 155                 160

Glu Tyr Met Lys Lys Ala Glu His Ser Arg Pro Pro Asn Glu Ala Gln
                165                 170                 175

Ile Ala Ala Gly His Ser Tyr Asp Pro Ala Cys His Gly Thr Asn Gly
            180                 185                 190

Thr Val Gln Ala Gly Pro Arg Asp Asn Gly Lys Pro Trp Ser Pro Ile
        195                 200                 205

Ile Lys Ala Leu Ile Asn Thr Ala Ser Glu Arg Gly Val Pro Thr Gln
    210                 215                 220

Gln Asp Phe His Cys Gly His Pro Arg Gly Val Ser Met Ile Pro Asn
225                 230                 235                 240
```

-continued

```
Ala Val His Glu Asp Gln Thr Arg Ser Asp Thr Ala Arg Glu Trp Leu
            245                 250                 255

Leu Pro Asn His Glu Arg Pro Asn Leu Lys Val Leu Thr Gly Gln Arg
        260                 265                 270

Val Gly Lys Val Leu Leu Asn Lys Thr Glu Ser Gly Ala Lys Ala Thr
    275                 280                 285

Gly Leu Asn Phe Gly Thr His Arg Lys Val Asn Tyr Asn Val Tyr Ala
290                 295                 300

Lys His Glu Val Leu Leu Ala Ala Gly Ser Ala Ile Ser Pro Leu Ile
305                 310                 315                 320

Leu Glu Trp Ser Gly Ile Gly Leu Lys Asp Val Leu Ser Ala Ala Gly
            325                 330                 335

Val Glu Gln Val Val Asp Leu Pro Val Gly Leu Asn Met Gln Asp Gln
        340                 345                 350

Thr Thr Thr Asn Val Arg Ser Gln Ala Gln Ala Ser Gly Ala Gly Gln
    355                 360                 365

Gly Gln Ala Val Tyr Phe Ala Ser Phe Asn Glu Thr Phe Gly Asp Tyr
370                 375                 380

Ala His Lys Ala Met Glu Leu Leu Asn Thr Lys Leu Asp Gln Trp Ala
385                 390                 395                 400

Glu Glu Thr Val Arg Asn Gly Gly Phe His Asn Val Thr Ala Leu Lys
            405                 410                 415

Ile Gln Tyr Glu Asn Tyr Arg Asp Trp Leu Leu Asn Glu Asp Val Ala
        420                 425                 430

Phe Ala Glu Leu Phe Leu Asp Thr Glu Gly Lys Ile Asn Phe Asp Leu
    435                 440                 445

Trp Asp Leu Ile Pro Phe Thr Arg Gly Ser Val His Ile Leu Asn Gly
450                 455                 460

Asp Pro Tyr Leu His Arg Tyr Ala Asn Asp Pro Lys Phe Phe Leu Asn
465                 470                 475                 480

Glu Phe Asp Ile Leu Gly Gln Ala Ala Ala Thr Lys Leu Ala Arg Glu
            485                 490                 495

Leu Ser Asn Thr Gly Glu Met Lys Lys Tyr Phe Ala Gly Glu Ile Ile
        500                 505                 510

Pro Gly Asp Asn Leu Ala Tyr Asp Ala Ser Leu Glu Gln Trp Ala Asp
    515                 520                 525

Tyr Val Lys Glu Asn Phe Arg Ala Asn Trp His Ala Val Ser Ser Cys
530                 535                 540

Ser Met Met Ser Arg Glu Met Gly Gly Val Val Asp Ser Ala Ala Arg
545                 550                 555                 560

Val Tyr Asp Val Glu Asn Leu Arg Ile Val Asp Gly Ser Ile Pro Pro
            565                 570                 575

Thr Gln Val Ser Ser His Val Met Thr Ile Phe Tyr Gly Met Ala Leu
        580                 585                 590

Lys Val Ala Asp Ala Ile Leu Ala Asp Tyr Ser Lys Asn
    595                 600                 605
```

<210> SEQ ID NO 5
<211> LENGTH: 587
<212> TYPE: PRT
<213> ORGANISM: Penicillium amagasakiense

<400> SEQUENCE: 5

```
Tyr Leu Pro Ala Gln Gln Ile Asp Val Gln Ser Ser Leu Leu Ser Asp
1               5                   10                  15

Pro Ser Lys Val Ala Gly Lys Thr Tyr Asp Tyr Ile Ile Ala Gly Gly
            20                  25                  30

Gly Leu Thr Gly Leu Thr Val Ala Ala Lys Leu Thr Glu Asn Pro Lys
        35                  40                  45

Ile Lys Val Leu Val Ile Glu Lys Gly Phe Tyr Glu Ser Asn Asp Gly
    50                  55                  60

Ala Ile Ile Glu Asp Pro Asn Ala Tyr Gly Gln Ile Phe Gly Thr Thr
65                  70                  75                  80

Val Asp Gln Asn Tyr Leu Thr Val Pro Leu Ile Asn Asn Arg Thr Asn
                85                  90                  95

Asn Ile Lys Ala Gly Lys Gly Leu Gly Gly Ser Thr Leu Ile Asn Gly
            100                 105                 110

Asp Ser Trp Thr Arg Pro Asp Lys Val Gln Ile Asp Ser Trp Glu Lys
        115                 120                 125

Val Phe Gly Met Glu Gly Trp Asn Trp Asp Asn Met Phe Glu Tyr Met
130                 135                 140

Lys Lys Ala Glu Ala Ala Arg Thr Pro Thr Ala Ala Gln Leu Ala Ala
145                 150                 155                 160

Gly His Ser Phe Asn Ala Thr Cys His Gly Thr Asn Gly Thr Val Gln
                165                 170                 175

Ser Gly Ala Arg Asp Asn Gly Gln Pro Trp Ser Pro Ile Met Lys Ala
            180                 185                 190

Leu Met Asn Thr Val Ser Ala Leu Gly Val Pro Val Gln Gln Asp Phe
        195                 200                 205

Leu Cys Gly His Pro Arg Gly Val Ser Met Ile Met Asn Asn Leu Asp
210                 215                 220

Glu Asn Gln Val Arg Val Asp Ala Ala Arg Ala Trp Leu Leu Pro Asn
225                 230                 235                 240

Tyr Gln Arg Ser Asn Leu Glu Ile Leu Thr Gly Gln Met Val Gly Lys
                245                 250                 255

Val Leu Phe Lys Gln Thr Ala Ser Gly Pro Gln Ala Val Gly Val Asn
            260                 265                 270

Phe Gly Thr Asn Lys Ala Val Asn Phe Asp Val Phe Ala Lys His Glu
        275                 280                 285

Val Leu Leu Ala Ala Gly Ser Ala Ile Ser Pro Leu Ile Leu Glu Tyr
290                 295                 300

Ser Gly Ile Gly Leu Lys Ser Val Leu Asp Gln Ala Asn Val Thr Gln
305                 310                 315                 320

Leu Leu Asp Leu Pro Val Gly Ile Asn Met Gln Asp Gln Thr Thr Thr
                325                 330                 335

Thr Val Ser Ser Arg Ala Ser Ser Ala Gly Ala Gly Gln Gly Gln Ala
            340                 345                 350

Val Phe Phe Ala Asn Phe Thr Glu Thr Phe Gly Asp Tyr Ala Pro Gln
        355                 360                 365

Ala Arg Asp Leu Leu Asn Thr Lys Leu Asp Gln Trp Ala Glu Glu Thr
370                 375                 380

Val Ala Arg Gly Gly Phe His Asn Val Thr Ala Leu Lys Val Gln Tyr
385                 390                 395                 400

Glu Asn Tyr Arg Asn Trp Leu Leu Asp Glu Asp Val Ala Phe Ala Glu
                405                 410                 415
```

```
Leu Phe Met Asp Thr Glu Gly Lys Ile Asn Phe Asp Leu Trp Asp Leu
            420                 425                 430

Ile Pro Phe Thr Arg Gly Ser Val His Ile Leu Ser Ser Asp Pro Tyr
        435                 440                 445

Leu Trp Gln Phe Ala Asn Asp Pro Lys Phe Phe Leu Asn Glu Phe Asp
450                 455                 460

Leu Leu Gly Gln Ala Ala Ser Lys Leu Ala Arg Asp Leu Thr Ser
465                 470                 475                 480

Gly Ala Met Lys Glu Tyr Phe Ala Gly Thr Leu Pro Gly Tyr
                485                 490                 495

Asn Leu Val Gln Asn Ala Thr Leu Ser Gln Trp Ser Asp Tyr Val Leu
                500                 505                 510

Gln Asn Phe Arg Pro Asn Trp His Ala Val Ser Ser Cys Ser Met Met
            515                 520                 525

Ser Arg Glu Leu Gly Gly Val Val Asp Ala Thr Ala Lys Val Tyr Gly
        530                 535                 540

Thr Gln Gly Leu Arg Val Ile Asp Gly Ser Ile Pro Pro Thr Gln Val
545                 550                 555                 560

Ser Ser His Val Met Thr Ile Phe Tyr Gly Met Ala Leu Lys Val Ala
                565                 570                 575

Asp Ala Ile Leu Asp Asp Tyr Ala Lys Ser Ala
                580                 585

<210> SEQ ID NO 6
<211> LENGTH: 606
<212> TYPE: PRT
<213> ORGANISM: Aspergillus nomius NRRL 13137

<400> SEQUENCE: 6

Met Lys Ser Val Ile Leu Ala Ser Thr Ile Ala Ser Val Ala Val Ala
1               5                   10                  15

Gln Ala Tyr Thr Ala Ala Glu Gln Ala Asn Val Gln Ala Asn Leu Ile
                20                  25                  30

Phe Asp Pro Lys Thr Val Ala Gly Lys Thr Val Asp Tyr Ile Ile Ala
            35                  40                  45

Gly Gly Gly Leu Thr Gly Leu Thr Val Ala Ala Lys Leu Thr Glu Asn
    50                  55                  60

Pro Asn Ile Asn Val Leu Val Ile Glu Lys Gly Phe Tyr Glu Ser Asn
65                  70                  75                  80

Asp Gly Pro Val Ile Glu Asn Pro Asn Asp Tyr Gly Leu Ile Phe Gly
                85                  90                  95

Ser Ser Val Asp His Asn Tyr Leu Thr Val Ser Gln Asp Ile Asn Asn
                100                 105                 110

Arg Thr Leu Asp Ile Lys Ala Gly Lys Gly Leu Gly Gly Ser Thr Leu
            115                 120                 125

Val Asn Gly Asp Ser Trp Thr Arg Pro Asp Lys Val Gln Ile Asp Ser
    130                 135                 140

Trp Glu Thr Val Phe Gly Asn Pro Gly Trp Asn Trp Asp Asn Leu Asn
145                 150                 155                 160

Asp Tyr Met Lys Lys Ala Glu Leu Ala Arg Tyr Pro Thr Gln Ala Glu
                165                 170                 175

Ile Ala Ala Gly His Tyr Phe Asn Ala Ser Cys His Gly Phe Asn Gly
            180                 185                 190

Thr Val His Ser Gly Pro Arg Asn Asp Gly Arg Pro Tyr Ser Val Leu
        195                 200                 205
```

```
Met Lys Ala Leu Met Asn Thr Thr Ala Ala Met Gly Val Pro Thr Gln
    210                 215                 220
Lys Asp Phe Leu Cys Gly His Pro Arg Gly Val Ser Met Ile Tyr Asn
225                 230                 235                 240
Asn Leu Leu Pro Asp Gln Thr Arg Ala Asp Ala Ala Arg Glu Trp Leu
                245                 250                 255
Leu Pro Asn Tyr Gln Arg Pro Asn Leu His Val Leu Thr Gly Gln Ile
                260                 265                 270
Val Gly Lys Val Leu Phe Asn Gln Thr Ser Ala Gly Pro Lys Ala Val
        275                 280                 285
Gly Val Asn Phe Gly Thr Asn Lys Ala Val Asn Phe Asn Val Tyr Ala
    290                 295                 300
Lys Tyr Glu Val Leu Leu Ala Ala Gly Ser Leu Val Ser Pro Leu Ile
305                 310                 315                 320
Leu Glu His Ser Gly Ile Gly Ile Lys Ser Val Leu Asp Gln Phe Asn
                325                 330                 335
Ile Thr Gln Leu Ile Glu Leu Pro Val Gly Leu Asn Met Gln Asp Gln
                340                 345                 350
Thr Thr Thr Thr Val Arg Ala Arg Ala Lys Ser Val Ala Ala Gly Gln
        355                 360                 365
Gly Gln Ala Val Tyr Phe Ala Asn Phe Thr Glu Val Phe Gly Asp Tyr
    370                 375                 380
Thr Pro Met Ala Val Gly Leu Leu Asn Asn Asn Leu Asp Gln Trp Ala
385                 390                 395                 400
Asn Glu Thr Val Ala Arg Gly Gly Phe His Asn Ala Thr Ala Leu Lys
                405                 410                 415
Ile Gln Tyr Glu Asn Tyr Arg Asn Trp Leu Leu Asn Glu Asp Val Ala
                420                 425                 430
Tyr Ala Glu Leu Phe Met Asp Thr Asn Gly Lys Ile Asn Phe Asp Leu
        435                 440                 445
Trp Asp Leu Ile Pro Phe Thr Arg Gly Ser Thr His Ile Thr Tyr Ala
    450                 455                 460
Asp Pro Tyr Leu Gln Ser Phe Ser Asn Asn Pro Arg Phe Leu Leu Asn
465                 470                 475                 480
Glu Leu Asp Leu Leu Gly Gln Ala Ala Ala Ser Met Leu Ala Arg Lys
                485                 490                 495
Leu Gln Asn Ser Gly Glu Met Ser Asn Tyr Phe Asp Gly Glu Asp Ile
                500                 505                 510
Pro Gly Ala Asp Leu Leu Ser Tyr Asn Ala Thr Leu Asp Asp Trp Val
        515                 520                 525
Gly Tyr Val Lys Gln Asn Phe Arg Ala Asn Trp His Ala Val Ser Thr
    530                 535                 540
Cys Ser Met Met Ser Lys Glu Leu Gly Gly Val Val Asp Pro Thr Ala
545                 550                 555                 560
Lys Val Tyr Gly Thr Leu Gly Leu Arg Val Ile Asp Gly Ser Val Ser
                565                 570                 575
Pro Thr Gln Val Ser Ser His Val Met Thr Ile Phe Tyr Gly Met Ala
                580                 585                 590
Leu Lys Ile Ala Asp Ala Ile Leu Ala Asp Tyr Asn Lys Ser
        595                 600                 605
```

<210> SEQ ID NO 7
<211> LENGTH: 602
<212> TYPE: PRT
<213> ORGANISM: Beauveria bassiana D1-5

<400> SEQUENCE: 7

```
Met Arg Phe Phe Ile Tyr Cys Gly Trp Leu Leu Ala Thr Thr Gly Ala
1               5                   10                  15

Tyr Leu Val Ser Glu Gln Val Asp Ile Gln Ala Ser Leu Leu Ile Asp
            20                  25                  30

Pro Lys Asp Val Ala Asp Lys Thr Phe Asp Tyr Ile Ile Ala Gly Gly
        35                  40                  45

Gly Leu Thr Gly Leu Thr Val Ala Ala Lys Leu Thr Glu Asn Pro Asn
    50                  55                  60

Ile Glu Val Leu Val Ile Glu Ala Gly Phe Tyr Glu Ser Asn Ser Gly
65                  70                  75                  80

Pro Val Ile Glu Asn Pro Asn Arg Tyr Gly Glu Val Phe Gly Thr Thr
                85                  90                  95

Val Asp His Asn Tyr Leu Thr Val Pro Leu Ile Asn Asn Arg Thr Asp
            100                 105                 110

Asn Ile Lys Ala Gly Lys Gly Leu Gly Gly Ser Thr Leu Ile Asn Gly
        115                 120                 125

Asn Ser Trp Thr Arg Pro Asp Lys Val Gln Ile Asp Ser Trp Glu Lys
    130                 135                 140

Val Phe Gly Asn Glu Gly Trp Thr Trp Asp Asn Ile Phe Pro Tyr Met
145                 150                 155                 160

Asn Arg Ala Glu Arg Ala Arg Ala Pro Thr Ala Val Gln Val Ala Ala
                165                 170                 175

Gly His Ser Phe Asp Pro Ala Cys His Gly Phe Asn Gly Thr Val His
            180                 185                 190

Ser Gly Pro Arg Asp Asn Gly Gln Pro Trp Ser Pro Leu Met Lys Ala
        195                 200                 205

Leu Met Asn Thr Thr Ser Ala Leu Gly Ala Pro Thr Gln Val Asp Phe
    210                 215                 220

Asn Cys Gly His Pro Arg Gly Val Ser Met Ile Pro Asn Asn Leu Leu
225                 230                 235                 240

Glu Asp Gln Val Arg Ala Asp Ala Ala Arg Glu Trp Leu Leu Pro Asn
                245                 250                 255

Tyr Arg Arg Lys Asn Leu Lys Val Leu Thr Gly His Ala Val Gly Lys
            260                 265                 270

Val Leu Phe Asp Gln Lys Ala Pro Ile Leu Lys Ala Ile Gly Val Asn
        275                 280                 285

Phe Gly Thr Asn Lys Ala Val Asn Phe Asn Ala Tyr Thr Lys His Glu
    290                 295                 300

Val Leu Leu Ala Ala Gly Ser Ser Ile Ser Pro Leu Ile Leu Glu Tyr
305                 310                 315                 320

Ser Gly Ile Gly Leu Lys Ser Val Leu Asp Lys Ala Asn Val Thr Gln
                325                 330                 335

Leu Val Glu Leu Pro Val Gly Ile Asn Met Gln Asp Gln Thr Thr Thr
            340                 345                 350

Thr Val Arg Ala Arg Ser Thr Ser Ala Gly Ala Gly Gln Gly Gln Ala
        355                 360                 365

Ile Tyr Phe Ala Asn Phe Thr Glu Thr Phe Gly Glu Asp Ile Ala Tyr
    370                 375                 380
```

```
Ala Thr Glu Leu Leu Glu Thr Lys Met Asp Gln Trp Ala Glu Thr
385                 390                 395                 400

Val Ala Arg Gly Gly Phe His Asn Val Thr Ala Leu Lys Val Gln Tyr
            405                 410                 415

Glu Asn Cys Arg Asp Trp Leu Leu His Glu Asp Val Ala Tyr Ala Glu
                420                 425                 430

Leu Phe Leu Asp Thr Ser Gly Gln Ile Asn Phe Asp Leu Trp Asp Leu
            435                 440                 445

Ile Pro Phe Thr Arg Gly Ser Thr His Ile Leu Ser Ser Glu Pro Tyr
        450                 455                 460

Arg Trp Gln Phe Ala Asn Asp Pro Lys Phe Phe Asn Glu Leu Asp
465                 470                 475                 480

Leu Leu Gly Gln Ala Ala Ala Thr Arg Leu Ala Arg Lys Leu Gln Asn
                485                 490                 495

Ser Gly Ala Met Ala Ser Tyr Phe Asp Gly Glu Val Ile Pro Gly Ala
                500                 505                 510

Glu Val Pro Glu Asp Ala Thr Leu Gly Gln Trp Ala Glu Tyr Val Lys
            515                 520                 525

Asp Asn Phe Arg Ala Asn Trp His Ala Val Gly Thr Cys Ser Met Met
530                 535                 540

Ser Arg Glu Leu Gly Gly Val Val Asp Ala Ala Ala Lys Val Tyr Asp
545                 550                 555                 560

Thr Gln Gly Leu Arg Val Ile Asp Gly Ser Ile Pro Pro Thr Gln Val
                565                 570                 575

Ser Ser His Val Met Thr Ile Phe Tyr Gly Met Ala Leu Arg Ile Ala
            580                 585                 590

Glu Ser Ile Leu Glu Asp Tyr Ala Lys Ser
        595                 600

<210> SEQ ID NO 8
<211> LENGTH: 604
<212> TYPE: PRT
<213> ORGANISM: Penicillium rubens Wisconsin 54-1255

<400> SEQUENCE: 8

Met Lys Ser Thr Ile Ile Thr Ser Ile Leu Phe Ser Val Ala Ala Val
1               5                   10                  15

Gln Ala Tyr Ser Pro Ala Glu Gln Ile Asp Val Gln Ser His Leu Leu
            20                  25                  30

Ser Asp Pro Thr Lys Val Glu Gly Glu Thr Tyr Asp Tyr Val Ile Ala
        35                  40                  45

Gly Gly Gly Leu Thr Gly Leu Thr Val Ala Ala Lys Leu Ser Glu Asn
    50                  55                  60

Pro Lys Ile Lys Val Leu Val Ile Glu Lys Gly Phe Tyr Glu Ser Asn
65                  70                  75                  80

Asp Gly Pro Ile Ile Glu Asp Pro Asn Ala Tyr Gly Glu Ile Phe Gly
                85                  90                  95

Thr Ser Val Asp Gln Asn Tyr Leu Thr Val Pro Leu Ile Asn Asn Arg
            100                 105                 110

Thr Gly Glu Ile Lys Ser Gly Leu Gly Leu Gly Gly Ser Thr Leu Ile
        115                 120                 125

Asn Gly Asp Ser Trp Thr Arg Pro Asp Lys Val Gln Ile Asp Ser Trp
    130                 135                 140

Glu Lys Val Phe Gly Met Glu Gly Trp Asn Trp Asp Asn Val Phe Gln
145                 150                 155                 160
```

-continued

```
Tyr Met Gln Lys Ala Glu Arg Ser Arg Pro Thr Ala Ala Gln Ile
                165                 170                 175
Glu Ala Gly His Phe Tyr Asp Pro Ala Cys His Gly Thr Asp Gly Thr
            180                 185                 190
Val His Ala Gly Pro Arg Asp Asn Gly Lys Pro Trp Ser Pro Leu Met
        195                 200                 205
Arg Ala Leu Met Asn Thr Val Ser Ala Phe Gly Val Pro Val Gln Lys
    210                 215                 220
Asp Phe His Cys Gly His Pro Arg Gly Val Ser Met Ile Pro Asn Asn
225                 230                 235                 240
Leu His Glu Asn Gln Ile Arg Ala Asp Ala Arg Glu Trp Leu Leu
            245                 250                 255
Pro Asn Tyr Gln Arg Asp Asn Leu Gln Ile Leu Thr Gly Gln Lys Val
            260                 265                 270
Gly Lys Val Leu Phe Asn Gln Thr Ala Ser Gly Pro Lys Ala Val Gly
    275                 280                 285
Val Asn Phe Gly Thr Asn Lys Ala Val Asn Phe Asn Val Tyr Ala Lys
    290                 295                 300
Gln Glu Val Leu Leu Ala Ala Gly Ser Ala Ile Ser Pro Leu Ile Leu
305                 310                 315                 320
Glu Tyr Ser Gly Ile Gly Ile Lys Ser Val Leu Asp Lys Ala Gly Val
            325                 330                 335
Lys Gln Leu Leu Glu Leu Pro Val Gly Leu Asn Met Gln Asp Gln Thr
            340                 345                 350
Thr Thr Thr Val Arg Ser Arg Ala Asn Asn Ala Pro Gly Gln Gly Gln
        355                 360                 365
Ala Ala Tyr Phe Ala Asn Phe Thr Glu Val Leu Gly Asp His Ala Ala
    370                 375                 380
Gln Gly Ile Lys Leu Leu Asp Thr Lys Leu Asp Gln Trp Ala Glu Glu
385                 390                 395                 400
Thr Val Ala Arg Gly Gly Phe His Asn Val Thr Ala Leu Lys Ile Gln
            405                 410                 415
Tyr Glu Asn Tyr Arg Asn Trp Leu Leu Asp Glu Asp Val Ala Phe Ala
            420                 425                 430
Glu Leu Phe Phe Asp Thr Glu Gly Lys Ile Asn Phe Asp Ile Trp Asn
        435                 440                 445
Leu Ile Pro Phe Thr Arg Gly Ser Val His Ile Leu Ser Ser Asp Pro
    450                 455                 460
Tyr Leu Trp Gln Tyr Ala Asn Asp Pro Lys Phe Phe Met Asn Glu Leu
465                 470                 475                 480
Asp Leu Leu Gly Gln Ala Ala Thr Lys Leu Gly Arg Glu Leu Ser
            485                 490                 495
Ser Ala Gly Glu Met Lys Lys Tyr Tyr Ala Gly Glu Thr Ile Pro Gly
        500                 505                 510
Asp Asn Leu Pro Gln Asp Ala Thr Val Glu Gln Trp Glu Asp Tyr Val
    515                 520                 525
Met Met Asn Phe Arg Pro Asn Trp His Ala Val Ser Thr Cys Ser Met
    530                 535                 540
Met Ser Arg Glu Leu Gly Gly Val Val Asp Ala Thr Ala Lys Val Tyr
545                 550                 555                 560
Gly Thr Gln Gly Leu Arg Val Ile Asp Gly Ser Ile Pro Pro Thr Gln
            565                 570                 575
```

Val Ser Ser His Val Met Thr Val Phe Tyr Gly Met Ala Leu Arg Ile
            580                 585                 590
Ala Glu Ser Val Leu Glu Asp Tyr Ala Lys Lys Ala
            595                 600

<210> SEQ ID NO 9
<211> LENGTH: 1770
<212> TYPE: DNA
<213> ORGANISM: Aspergillus niger

<400> SEQUENCE: 9

| | | | | | |
|---|---|---|---|---|---|
| ctgccacact | acatcaggag | caatggcatt | gaagccagcc | tcctgactga | tcccaaggat | 60 |
| gtctccggcc | gcacggtcga | ctacatcatc | gctggtggag | gtctgactgg | actcaccacc | 120 |
| gctgctcgtc | tgacggagaa | ccccaacatc | agtgtgctcg | tcatcgaaag | tggctcctac | 180 |
| gagtcggaca | gaggtcctat | cattgaggac | ctgaacgcct | acggcgacat | ctttggcagc | 240 |
| agtgtagacc | acgcctacga | gaccgtggag | ctcgctacca | caatcaaac | cgcgctgatc | 300 |
| cgctccggaa | atggtctcgg | tggctctact | ctagtgaatg | gtggcacctg | gactcgcccc | 360 |
| cacaaggcac | aggttgactc | ttgggagact | gtctttggaa | atgagggctg | gaactgggac | 420 |
| aatgtggccc | cctactccct | ccaggctgag | cgtgctcgcg | caccaaatgc | caaacagatc | 480 |
| gctgctggcc | actacttcaa | cgcatcctgc | catggtgtta | atggtactgt | ccatgccgga | 540 |
| ccccgcgaca | ccggcgatga | ctattctccc | atcgtcaagg | ctctcatgag | cgctgtcgaa | 600 |
| gaccggggcg | ttcccaccaa | gaaagacttc | ggatgcggtg | accccatgg | tgtgtccatg | 660 |
| ttccccaaca | ccttgcacga | agaccaagtg | cgctccgatg | ccgctcgcga | atggctactt | 720 |
| cccaactacc | aacgtcccaa | cctgcaagtc | ctgaccggac | agtatgttgg | taaggtgctc | 780 |
| cttagccaga | acggcaccac | ccctcgtgcc | gttggcgtgg | aattcggcac | ccacaagggc | 840 |
| aacacccaca | acgtttacgc | taagcacgag | gtcctcctgg | ccgcgggctc | cgctgtctct | 900 |
| cccacaatcc | tcgaatattc | cggtatcgga | atgaagtcca | tcctggagcc | ccttggtatc | 960 |
| gacaccgtcg | ttgacctgcc | cgtcggcttg | aacctgcagg | accagaccac | cgctaccgtc | 1020 |
| cgctcccgca | tcacctctgc | tggtgcagga | cagggacagg | ccgcttggtt | cgccaccttc | 1080 |
| aacgagacct | tggtgactta | tccgaaaaag | gcacacgagc | tgctcaacac | caagctggag | 1140 |
| cagtgggccg | aagaggccgt | cgcccgtggc | ggattccaca | acaccaccgc | cttgctcatc | 1200 |
| cagtacgaga | actaccgcga | ctggattgtc | aaccacaacg | tcgcgtactc | ggaactcttc | 1260 |
| ctcgacactg | ccggagtagc | cagcttcgat | gtgtgggacc | ttctgccctt | cacccgagga | 1320 |
| tacgttcaca | tcctcgacaa | ggaccctac | cttcaccact | tcgcctacga | ccctcagtac | 1380 |
| ttcctcaacg | agctggacct | gctcggtcag | gctgccgcta | tcaactggcc | cgcaacatc | 1440 |
| tccaactccg | gtgccatgca | gacctacttc | gctggggaga | ctatcccgg | tgataacctc | 1500 |
| gcgtatgatg | ccgatttgag | cgcctggact | gagtacatcc | cgtaccactt | ccgtcctaac | 1560 |
| taccatggcg | tgggtacttg | ctccatgatg | ccgaaggaga | tgggcggtgt | tgttgataat | 1620 |
| gctgcccgtg | tgtatggtgt | gcagggactg | cgtgtcattg | atggttctat | tcctcctacg | 1680 |
| caaatgtcgt | cccatgtcat | gacggtgttc | tatgccatgg | cgctaaaaat | ttcggatgct | 1740 |
| atcttggaag | attatgcttc | catgcagtga | | | | 1770 |

<210> SEQ ID NO 10
<211> LENGTH: 5
<212> TYPE: PRT
<213> ORGANISM: Artificial Sequence

```
<220> FEATURE:
<223> OTHER INFORMATION: Motif 1
<220> FEATURE:
<221> NAME/KEY: misc_feature
<222> LOCATION: (2)..(3)
<223> OTHER INFORMATION: Xaa can be any naturally occurring amino acid

<400> SEQUENCE: 10

Glu Xaa Xaa Pro Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Motif 2
<220> FEATURE:
<221> NAME/KEY: MISC_FEATURE
<222> LOCATION: (3)..(3)
<223> OTHER INFORMATION: Xaa=Ala or Thr
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa=Arg or Ala
<220> FEATURE:
<221> NAME/KEY: MISC_FEATURE
<222> LOCATION: (9)..(9)
<223> OTHER INFORMATION: Xaa=Ile or Ala
<220> FEATURE:
<221> NAME/KEY: MISC_FEATURE
<222> LOCATION: (10)..(10)
<223> OTHER INFORMATION: Xaa=Thr or Ser

<400> SEQUENCE: 11

Thr Thr Xaa Thr Val Xaa Ser Xaa Xaa Xaa
1               5                   10
```

MUTANT GLUCOSE OXIDASE AND USE THEREOF

SEQUENCE LISTING SUBMISSION VIA EFS-WEB

A computer readable text file, entitled "SequenceListing.txt," created on or about Sep. 25, 2020 with a file size of about 43 kb contains the sequence listing for this application and is hereby incorporated by reference.

BACKGROUND OF THE INVENTION

Field of the Invention

The present invention relates to a method for giving a new function to glucose oxidase by introduction of a site-directed mutation, and a glucose oxidase having a mutation introduced therein.

Description of the Related Art

Biosensors using glucose oxidase (GOX) has been developed for a long time. First, the so-called first generation type, which is described in Non-patent Document 1, has been developed. In this method, the product of the side reaction $O_2 \rightarrow H_2O_2$, which occurs due to the oxidation reaction of glucose in the system, is oxidized with a platinum electrode or the like to allow measurement of the glucose concentration. This was followed by development of the second generation type, wherein electron transfer between GOX and an electrode is mediated by an electron acceptor (mediator) added to the system, without being dependent on the instable $O_2$ or $H_2O_2$ (Non-patent Document 2). Non-patent Document 3 showed that detection of electrons from the glucose oxidation reaction is possible even without addition of an electron acceptor when a carbon nanoparticle such as graphene is used in combination.

In Non-patent Document 4 and Patent Document 1, the present inventors disclosed the 2.5th generation type, wherein direct monitoring of electron transfer is possible by chemical modification of the molecular surface of glucose dehydrogenase (GDH) or the like with an electron acceptor.

PRIOR ART DOCUMENTS

Patent Document

[Patent Document 1] WO 2018/062542

Non-Patent Documents

[Non-patent Document 1] Clin Chem 1978, 24 (1) 150-152
[Non-patent Document 2] Biosensors 1989, 4 (2) 109-119
[Non-patent Document 3] Mater Sci Eng C Mater Biol Apple 2017 Jul. 1; 76, 398-405
[Non-patent Document 4] Bioelectrochemistry 2018 June, 121: 185-190

SUMMARY OF THE INVENTION

Since glucose oxidase has better thermal stability and substrate specificity compared to GDH, it may be useful for preparation of a stable, highly accurate biosensor if the glucose oxidase molecule itself can be modified to allow easier electron transfer with an electrode even without addition of a free electron acceptor to the reaction system.

However, application of glucose oxidase to a glucose sensor is not easy. This is because of the following problems. First-generation sensors require application of a high voltage. Second-generation sensors, which are systems based on detection of an electron acceptor, are affected by interference of the dissolved oxygen level in the sample. Third-generation sensors of the direct electron transfer type need to be designed such that easy access of the electrode to the active site of the enzyme is secured, so that preparation of the electrode is very complicated, leading to difficulty in control.

Although Non-patent Document 4 and Patent Document 1 disclose chemical modification of GDH with an electron acceptor, application of this technique to glucose oxidase has not been easy.

In order to prepare glucose oxidase as an enzyme capable of direct electron transfer, the present inventors studied chemical modification with an electron acceptor. During the course of this study, random modification of side-chain amino groups present in the amino acid sequence of glucose oxidase with an electron acceptor resulted in the absence of direct electron transfer. In view of this, a detailed study was carried out to identify the amino acid to be modified with the electron acceptor based on the spatial structure of glucose oxidase, structural similarity of glucose oxidase to GDH, and the like, and mutations were introduced to glucose oxidase.

As a result, an amino acid residue (amino acid residue corresponding to the isoleucine at position 489 or the arginine at position 335 in the amino acid sequence of SEQ ID NO:1) close to the FAD-binding site, which is the active center of glucose oxidase, was substituted with a lysine residue for modification with an electron acceptor, to obtain a mutant glucose oxidase. Thereafter, the amino group in the side chain of the lysine residue introduced in the resulting mutant glucose oxidase was covalently bound to an electron acceptor by chemical modification. The modified glucose oxidase mutant obtained was found to have a specific electron transfer ability that cannot be achieved with wild-type glucose oxidase, and it was found that sensors with an enzyme electrode using this enzyme show responses to glucose even without addition of a free electron acceptor from outside. Based on such discoveries, the present invention was completed.

The present invention can be summarized as follows.

[1] A mutant glucose oxidase comprising an amino acid sequence in which a residue corresponding to isoleucine at position 489 or arginine at position 335 in the amino acid sequence of SEQ ID NO:1 is substituted with an amino acid residue having a reactive functional group in a side chain.

[2] The mutant glucose oxidase according to [1], wherein the amino acid residue having a reactive functional group in the side chain is a lysine residue.

[3] The mutant glucose oxidase according to [1] to [2], wherein said mutant glucose oxidase has an amino acid sequence with a sequence identity of not less than 90% to the amino acid sequence of any one of SEQ ID NOs:1 to 8.

[4] The mutant glucose oxidase according to any one of [1] to [3], wherein said mutant glucose oxidase originates from *Aspergillus niger*.

[5] An (artificial) electron acceptor-modified glucose oxidase obtained or obtainable by introducing an electron acceptor to the mutant glucose oxidase according to any one of [1] to [4], wherein the electron acceptor has been introduced to the glucose oxidase through the amino acid residue having a reactive functional group in the side chain.

[6] The electron acceptor-modified glucose oxidase according to [5], wherein the electron acceptor is a phenazinium compound.

[7] The electron acceptor-modified glucose oxidase according to [6], wherein the phenazinium compound is represented by the following formula:

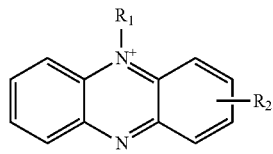

wherein $R_1$ represents a hydrocarbyl group, and $R_2$ represents a linker.

[8] An enzyme electrode comprising an electrode base material and the electron acceptor-modified glucose oxidase according to any one of [5] to [7] bound to the base material.

[9] A biosensor comprising the enzyme electrode according to [8].

[10] A method of preparing an electron acceptor-modified glucose oxidase comprising introducing an electron acceptor to a mutant glucose oxidase as defined in any one of [1] to [4], wherein the electron acceptor is introduced to the glucose oxidase through the amino acid residue having a reactive functional group in the side chain.

[11] The method according to [10] wherein the electron acceptor is as defined in [6] or [7].

Conventionally, while glucose oxidase had an advantage over GDH in terms of its thermal stability and substrate specificity as an element for glucose measurement, detection of a signal by the electrode required addition of an electron acceptor as an electron acceptor from outside. It was found, however, that use of the mutant enzyme according to the present invention enables construction of a sensor having a minimal configuration composed only of an enzyme and electrodes, without addition of the electron acceptor from outside. By using the electron acceptor-modified glucose oxidase obtained by the present invention, a stable biosensor having a high substrate specificity can be simply prepared.

DETAILED DESCRIPTION OF THE INVENTION

<Mutant Glucose Oxidase>

Figure 1:
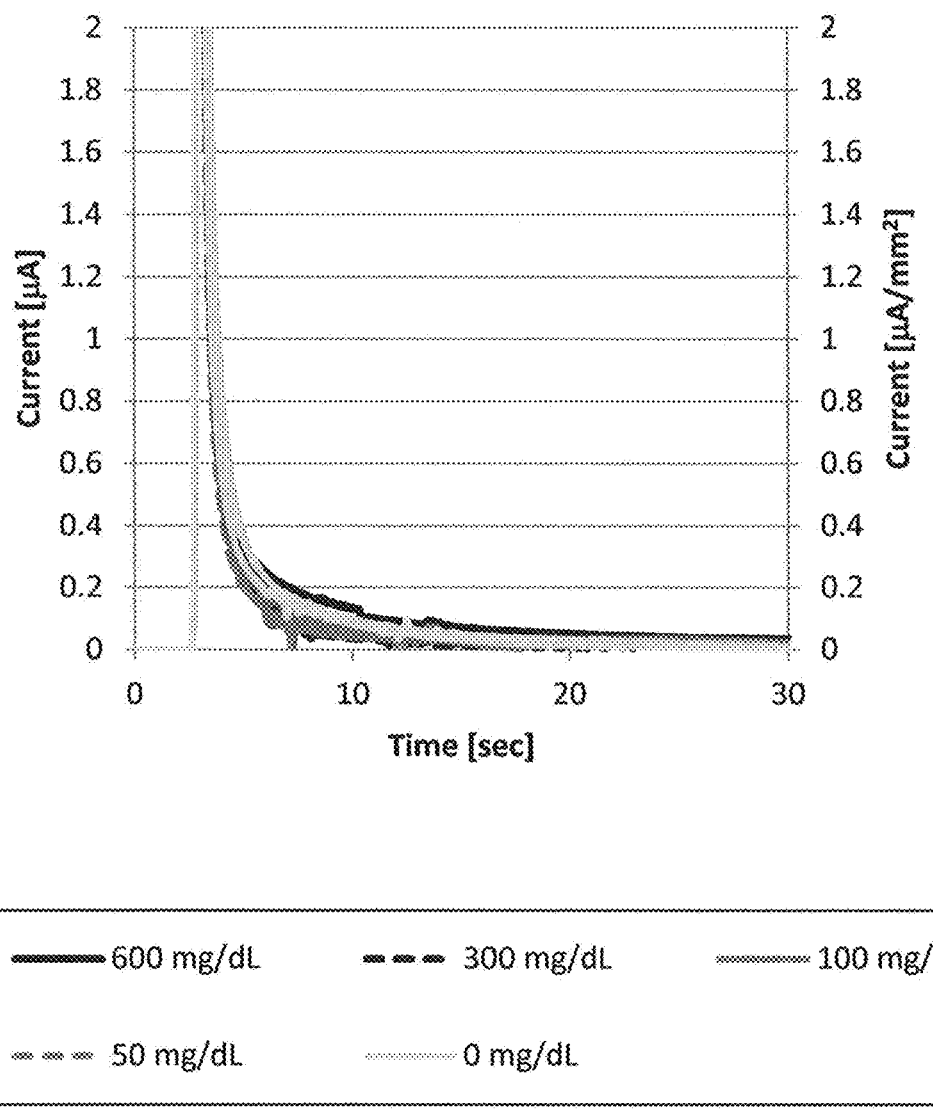
FIG. 1 shows a graph showing results of amperometric measurement using a sensor including a PES-modified enzyme obtained by modifying wild-type GOX with PES.

In the mutant glucose oxidase of the present invention, the amino acid residue corresponding to the isoleucine at position 489 or the arginine at position 335 in the amino acid sequence of SEQ ID NO:1 is substituted with an amino acid residue having a reactive functional group in the side chain.

Since these amino acid residues are positioned close to the binding site of a coenzyme FAD and the substrate pocket in the spatial structure of glucose oxidase, modification with the later-mentioned electron acceptor through these amino acid residues allows the glucose oxidase to function as a direct electron transfer-type oxidoreductase.

Examples of the amino acid residue having a reactive functional group in the side chain include lysine, which has an amino group in the side chain, glutamic acid and aspartic acid, each of which has a carboxyl group in the side chain, and cysteine, which has a thiol group in the side chain.

The mutant glucose oxidase of the present invention may originate from *Aspergillus niger* and thus may be obtained by modifying a sequence of glucose oxidase from *Aspergillus niger*. SEQ ID NO:1 is the amino acid sequence of glucose oxidase derived from the *Aspergillus niger* NRRL3 strain (mature type), and examples of the mutant glucose oxidase include a mutant glucose oxidase having the same amino acid sequence as SEQ ID NO:1 except that the isoleucine at position 489 or the arginine at position 335 is substituted with an amino acid residue having a reactive functional group in the side chain, such as lysine.

However, in the mutant glucose oxidase, as long as the isoleucine at position 489 or the arginine at position 335 in the amino acid sequence of SEQ ID NO:1 is substituted with an amino acid residue having a reactive functional group in the side chain, such as lysine, and as long as the mutant glucose oxidase has glucose oxidase activity, the amino acids other than those at positions 489 and 335 in SEQ ID NO:1 do not need to be the same as in SEQ ID NO:1, and may have one or several amino acid substitution(s), deletion(s), insertion(s), addition(s), and/or the like. The term "one or several" herein means 1 to 50, 1 to 20, 1 to 10, or 1 to 5 (the same applies hereinafter).

In the mutant glucose oxidase of the present invention, as long as the isoleucine at position 489 or the arginine at position 335 in the amino acid sequence of SEQ ID NO:1 is substituted with an amino acid residue having a reactive functional group in the side chain, such as lysine, and as long as the mutant glucose oxidase has glucose oxidase activity, the mutant glucose oxidase of the present invention may also be a protein having a sequence identity of not less than 90%, not less than 95%, or not less than 98% to the amino acid sequence of SEQ ID NO:1. The amino acid sequence identity herein can be defined by aligning two amino acids such that the number of matched amino acids is maximum while inserting a gap(s) when necessary, and calculating the ratio of the number of matched amino acids to the total number of amino acids in the aligned portion (the same applies hereinafter).

The mutant glucose oxidase of the present invention may also be a mutant glucose oxidase having the same amino acid sequence as the amino acid sequence of a glucose oxidase derived from another organism except that the amino acid residue corresponding to the isoleucine at position 489 or the arginine at position 335 in the amino acid sequence of SEQ ID NO:1 is substituted with an amino acid residue having a reactive functional group in the side chain.

The other amino acid sequence is not limited as long as it is an amino acid sequence of a glucose oxidase protein having an amino acid residue corresponding to the isoleucine at position 489 (I489) or the arginine at position 335 (R335) in the amino acid sequence of SEQ ID NO:1. Examples of such an amino acid sequence include the amino acid sequences of SEQ ID NOs:2 to 8 described in the following Table 1. In Table 1, the amino acid residues corresponding to I489 and R335 are shown for each amino acid sequence.

Accordingly, other examples of the mutant glucose oxidase of the present invention include proteins each having the same amino acid sequence as any one of SEQ ID NOs:2 to 8 except that the amino acid residue corresponding to the isoleucine at position 489 or the arginine at position 335 in the amino acid sequence of SEQ ID NO:1 is substituted with an amino acid residue having a reactive functional group in the side chain.

In the mutant glucose oxidase of the present invention, as long as the amino acid residue corresponding to the isoleucine at position 489 or the arginine at position 335 in the amino acid sequence of SEQ ID NO:1 is substituted with a lysine residue, and as long as the mutant glucose oxidase has glucose oxidase activity, the mutant glucose oxidase of the present invention may also be a protein having the same amino acid sequence as any one of SEQ ID NOs:2 to 8 except that the amino acid sequence has one or several amino acid substitution(s), deletion(s), insertion(s), addition(s) (as described hereinbefore), and/or the like, or a protein having a sequence identity of not less than 90%, not less than 95%, or not less than 98% to the amino acid sequence of any one of SEQ ID NOs:2 to 8.

TABLE 1

| Accession No. | R335 | I489 | SEQ ID NO: | Microorganism |
| --- | --- | --- | --- | --- |
| 1CF3 | R335 | I489 | 1 | *Aspergillus niger* |
| OQD69692.1 | R357 | V511 | 2 | *Penicillium polonicum* |
| OQD69251.1 | A363 | I517 | 3 | *Penicillium polonicum* |
| XP_002375824.1 | R358 | I512 | 4 | *Aspergillus flavus* |
| 1GPE | S339 | L493 | 5 | *Penicillium amagasakiense* |
| XP_015407838.1 | R358 | I512 | 6 | *Aspergillus nomius* |
| KGQ09389.1 | R355 | I509 | 7 | *Beauveria bassiana* |
| XP_002563451.1 | R357 | I510 | 8 | *Penicillium rubens* |

The "amino acid residue corresponding to the isoleucine at position 489 or the arginine at position 335 in the amino acid sequence of SEQ ID NO:1" can be identified by alignment of the amino acid sequence of SEQ ID NO:1 with the subject amino acid sequence.

Examples of the alignment are shown in Tables 2 and 3.

The arrows in these tables indicate the "amino acid residue corresponding to the isoleucine at position 489 in the amino acid sequence of SEQ ID NO:1" and the "amino acid residue corresponding to the arginine at position 335 in the amino acid sequence of SEQ ID NO:1", respectively.

In these tables, P13006.1 shows a sequence of the 1CF3 precursor, and AAD01493.1 shows a sequence of the 1GPE precursor.

The amino acid residue corresponding to the isoleucine at position 489 in the amino acid sequence of SEQ ID NO:1 is the amino acid corresponding to $X_2$ in the following amino acid sequence motif, and can therefore also be identified based on the presence of this motif in the subject amino acid sequence.

Glu-$X_1$-$X_2$-Pro-Gly (SEQ ID NO: 10)

More specifically, this amino acid residue is V511 in SEQ ID NO:2, T517 in SEQ ID NO:3, I512 in SEQ ID NO:4, L493 in SEQ ID NO:5, I512 in SEQ ID NO:6, I509 in SEQ ID NO:7, and I510 in SEQ ID NO:8.

TABLE 2

| | | |
|---|---|---|
| 1CF3 | ELDLLGQAAATQLARNISNSGAMQTYFAGETIPGDNLA-YDADLSAWTEYIPYHFRPNYHGVGTCSMMPKEMGGVVDNAARVYGVQGLRVIDGSIPPTQM | 556 |
| P13006.1 | ELDLLGQAAATQLARNISNSGAMQTYEAGETIPGDNLA-YDADLSAWTEYIPYHFRPNYHGVGTCSMMPKEMGGVVDNAARVYGVQGLRVIDGSIPPTQM | 578 |
| CQD69692.1 | ELDLLGQAAASKLAREISNKGEMTKYENSETVPGNNLA-YDATLDQWVDYVRQNFRPNYHGVGTCSMMSKELGGVVDAAARVYGLRVIDGSIPPTQV | 578 |
| CQD69251.1 | DLDLLGQAAGSKLAREISNSGDMQTYFDGETTPGDNLE-YDADLLQWVDYVKQNFRANWHAVGTCSMNAKELGGVVDSEARVYGVEGLRVIDGSIPPTQV | 584 |
| XP_002375824.1 | EFDILGQAAATKLARELSNTGEMKKYFAGEIIPGDNLA-YDASLEQWADYVRENFRANWHAVSSCSMMSREMGGVVDSAARVYDVENLRIVDGSIPPTQV | 579 |
| 1GPE | EFDLLGQAAASKLARDLTSGGAMKEYEAGETLPGYNLV-QNATLSQWSDYVLQNFRPNWHAVSSCSMNSRELGGVVDATARVYGTQGLRVIDGSIPPTQV | 560 |
| AAD01493.1 | EFDLLGQAAASKLARDLTSQGAMKEYFAGETLPGYNLV-QNATLSQWSDYVLQNFRPNWHAVSSCSMNSRELGGVVDATARVYGTQGLRVIDGSIPPTQV | 578 |
| XP_015407838.1 | ELDLLGQAAASMLARKLGNSGEMSNYEDGEDIPGADLLSYNATLDDWVGYVKQNFRANWHNVSTCSMNSKELGGVVDPTAKVZGTLGLRVIDGSVSPTQV | 580 |
| KGQ09389.1 | ELDLLGQAAATRLARKLGNSGAMASYEDGEVIPGAEVP-EDATLGQWAEYVKDNFRANWHAVGECSMNSRELGGVVDAAARVYDTQGLRVIDGSIPPTQV | 576 |
| XP_002563451.1 | ELDLLGQAAATKLGRELSSAGEMKKYYAGETIPGDNLP-QDATVEQMEDYVMMNFRPNWHAVSTCSMMSRELGGVVDATAKVYGTQGLRVIDGSIPPTQV | 577 |

The amino acid residue corresponding to the arginine at position 335 in the amino acid sequence of SEQ ID NO:1 is the amino acid corresponding to X in the following amino acid sequence motif, and can therefore also be identified based on the presence of this motif in the subject amino acid sequence.

TT(A/T)TVXS(R/A)(I/A)(T/S) (SEQ ID NO: 11)

More specifically, this amino acid residue is R357 in SEQ ID NO:2, A363 in SEQ ID NO:3, R358 in SEQ ID NO:4, 5339 in SEQ ID NO:5, R358 in SEQ ID NO:6, R355 in SEQ ID NO:7, and R357 in SEQ ID NO:8.

TABLE 3

| | | |
|---|---|---|
| 1CF3 | VEFG-THKGNTHNVYAKHEVLLAAGSAVSPTILEYSGIGMKSILEPLGIDTVVDLP-VGLNLQDQTTATVRSRITSAGAGQGQAAWFAT--FNETFGDYS | 362 |
| P13006.1 | VEFG-THKGNTHNVYAKHEVLLAAGSAVSPTILEYSGIGNESILEPLGIDTVVDLP-VGLNLQDQTTATVRSRITSAGAGQGQAAWFAT--FNETEGDYS | 384 |
| CQD69692.1 | VNFG-THNKVNFDVHAKHEVLLAAGSTVSPCILEHSGVGLKTVLDRVGVKQLVELP-VGLNLQDQTTTTVRSAINPIGAGQGQAAYFAT--FBETFGDQA | 384 |
| CQD69251.1 | VNFG-TNKNVNFNVYAKHEVLLAASGSVVSPRILEYSGIGLKSVLDTAGIQQIVDLP-VGLNMQDQTTTTVASRIKSSGNGQGQAIYFAT--FNETEGDYA | 390 |
| XP_002375824.1 | LNFG-THRKVNYNVYAKHEVLLAAGSAISPLILEWSGIGLKDVLSAAGVEQVVDLP-VGLNMQDQTTNVRSQAQASGAGAGQGQAVYFAS--FNETEGDYA | 385 |
| 1GPE | VNFG-TNKAVNFDVFAKHEVLLAAGSAISPLILEYSGIGLKSVLDQANVTQLLDLP-VGINMQDQTTTTVSSRASSAGAGQGQAVFFAN--FTETFGDYA | 366 |
| AAD01493.1 | VNFG-TNKAVNFDVFAKHEVLLAAGSAISPLILEYSGIGLKSVLDCANVTQLLDLP-VGINMQDQTTTTVSSRASSAGAGQGQAVFFAN--FTETFGDYA | 384 |
| XP_015407838.1 | VNFG-TNKAVNFNVYAKYEVLLAAGSLVSPLILEHSGIGIKSVLDQFNITQLIELP-VGLNMQDQTTTVRARAKSVAAGQGQAVIFAN--FTEVFGDYT | 385 |
| KGQ09389.1 | VNFG-TNKAVNFNAYTKHEVLLAAGSSISPLILEYSGIGLRSVLDRANVTQLVELP-VGINMQDQTTTVRARSTSAGAGQGQAIYFAN--FTETFGEDI | 382 |
| XP_002563451.1 | VNFG-TNKAVNFNVYAKQEVLLAAGSAISPLILEYSGIGIKSVLDKAGVKQLLELP-VGLNMQDQTTTTVRSRANNA-PGQGQAAYFAN--FTEVLGDHA | 383 |

In the mutant glucose oxidase of the present invention, glucose oxidase activity is maintained.

The "glucose oxidase activity" herein means an enzymatic activity that catalyzes oxidation of glucose using oxygen as an electron acceptor, to produce gluconolactone. The glucose oxidase activity can be measured by, for example, using glucose as a substrate, and an electron acceptor such as (3-(4, 5-dimethylthiazol-2-yl)-2, 5-diphenyltetrazolium bromide) (MTT) or 1-methoxy phenazine methosulfate (PMS) instead of oxygen, as described below in the Examples. For example, the glucose oxidase activity of the mutant glucose oxidase is not less than 10%, not less than 20%, or not less than 50% as compared to the activity of a wild type glucose oxidase.

The mutant glucose oxidase can be prepared by a known genetic recombination method such as site-directed mutagenesis. More specifically, by obtaining a DNA encoding glucose oxidase, introducing a site-specific mutation thereto using, for example, a primer for introduction of the mutation, allowing expression from the resulting DNA in an appropriate host to produce a mutant glucose oxidase, and then purifying the mutant glucose oxidase as required, the mutant glucose oxidase can be obtained.

The DNA encoding the glucose oxidase can be obtained from a desired gene source such as *Aspergillus niger* by a method such as PCR. Primers for the PCR can be prepared by chemical synthesis based on a known base sequence. Alternatively, the DNA can be obtained by hybridization using, as a probe, an oligonucleotide prepared based on a known base sequence.

The gene encoding the mutant glucose oxidase (mutant GOX gene) is not limited as long as it has a base sequence corresponding to the amino acid sequence of the mutant glucose oxidase described above. Specific examples of the gene include a DNA containing the same base sequence as the base sequence of SEQ ID NO:9 except that it has a codon substitution corresponding to the above amino acid substitution. The mutant GOX gene may be a DNA having the base sequence of SEQ ID NO:9, or a DNA which hybridizes, under stringent conditions, with a probe that can be prepared from this sequence, and which encodes a protein having glucose oxidase activity.

Examples of the stringent conditions described above include conditions that allow hybridization of DNAs having an identity of preferably 80%, more preferably not less than 90%, especially preferably not less than 95%, with each other. More specifically, for example, such conditions are achieved by washing with 0.1×SSC and 0.1% SDS at 60° C.

By incorporating the resulting DNA into a vector that can function in a host cell, transforming the host cell with this vector, and then allowing expression from the DNA, a mutant glucose oxidase can be produced.

The vector(s) to be used for the acquisition of the glucose oxidase gene, the introduction of the mutation, the expression of the gene, and the like may be appropriately selected depending on the host, and specific examples of such vectors include those which can function in bacteria belonging to the genus *Escherichia*, such as pTrc99A, pBR322, pUC18, pUC118, pUC19, pUC119, pACYC184, pBBR122, and pET. The promoter to be used for the expression of the gene may also be appropriately selected depending on the host, and examples of the promoter include those which can function in bacteria belonging to the genus *Escherichia*, such as lac, trp, tac, trc, PL, and tet.

Examples of the method for the transformation of the host cell with the recombinant vector include the competent cell method by calcium treatment, the lipofection method, the protoplast method, and the electroporation method.

Examples of the host cell include intestinal bacteria such as bacteria belonging to the genus *Escherichia*; bacteria belonging to the genus *Bacillus*, such as *Bacillus subtilis*; yeasts such as *Saccharomyces cerevisiae*; filamentous fungi such as *Aspergillus niger*; mammalian cells; and insect cells. The host cell is not limited to these, and any host cell may be used as long as it is suitable for production of a foreign protein.

By culturing the host cell under appropriate conditions, the mutant glucose oxidase can be produced as a recombinant protein. Purification of the mutant glucose oxidase can be carried out by a known method such as column chromatography. In cases where the mutant glucose oxidase contains a tag sequence for purification, the purification is also possible by, for example, affinity chromatography for the tag.

<Modification with Electron Acceptor>

The electron acceptor-modified glucose oxidase of the present invention comprises an electron acceptor which is bound to the above-mentioned mutant glucose oxidase through the amino acid residue having a reactive functional group in the side chain.

The electron acceptor herein is not limited as long as it is a compound having no catalytic action and receives an electron from an oxidoreductase to undergo reduction, followed by reoxidation in the electrode. Examples of the electron acceptor include phenazinium compounds, ferrocene, quinone compounds (for example, 1,4-naphthoquinone, 2-methyl-1,4-naphtoquinone, 9,10-phenanthrenequinone, 1,2-naphthoquinone, p-xyloquinone, methylbenzoquinone, 2,6-dimethylbenzoquinone, sodium 1,2-naphthoquinone-4-sulfonate, 1,4-anthraquinone, 9,10-anthraquinone, tetramethylbenzoquinone, and thymoquinone); phenylenediamine compounds (for example, N,N-dimethyl-1,4-phenylenediamine and N,N,N',N'-tetramethyl-1,4-phenylenediamine dihydrochloride), coenzyme Q0, AZURE A chloride, phenosafranin, 6-aminoquinoxaline, toluidine blue, and tetrathiafulvalene.

Examples of the phenazinium compounds (to be introduced/bound to the mutant GOX) include the compounds represented by the following formula, such as 5-methylphenazinium and 5-ethylphenazinium.

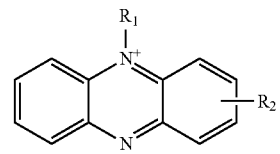

$R_1$ represents a hydrocarbyl group, and may be a saturated hydrocarbyl group, unsaturated hydrocarbyl group, or aromatic hydrocarbyl group. The number of carbons in the hydrocarbyl group is, for example, 1 to 10. By way of example the hydrocarbyl group may be an alkyl group, e.g. with 1 to 6 carbons.

$R_2$ represents a linker that links the phenazinium skeleton to the side chain of the glucose oxidase, and examples of $R_2$ include an alkylene group or an alkenylene group that may have a heteroatom such as an oxygen atom, sulfur atom, or nitrogen atom in the main chain or a side chain. The number of atoms in the main chain of the linker is, for example, 1 to 20, or 1 to 10. The linker includes at its end the residue for binding to the side chain of the glucose oxidase.

The invention also provides a method of preparing an electron acceptor-modified glucose oxidase comprising introducing an electron acceptor to the mutant glucose oxidase as defined hereinbefore, wherein the electron acceptor is introduced to the glucose oxidase through the amino acid residue having a reactive functional group in the side chain. As referred to herein the introduction results in the electron acceptor binding to the mutant glucose oxidase thereby modifying the enzyme. Examples of the method for the modification of the glucose oxidase with the electron acceptor include a method in which a functional group such as succinimide is introduced to the above-described electron acceptor, and the functional group is then allowed to react with the side-chain amino group of a lysine residue introduced in the mutant glucose oxidase, to achieve the modification.

Examples of the method also include a method in which a functional group such as maleimide is introduced to the above-described electron acceptor, and the functional group is then allowed to react with the side-chain thiol group of a cysteine residue introduced in the mutant glucose oxidase, to achieve the modification.

Examples of the method also include a method in which a functional group such as oxazoline is introduced to the above-described electron acceptor, and the functional group is then allowed to react with the side-chain carboxyl group of a glutamic acid or aspartic acid residue introduced in the mutant glucose oxidase, to achieve the modification.

A cross-linking agent may be used in addition.

In cases where the modification is carried out with phenazine ethosulfate (PES), examples of the method include a method in which a compound prepared by introducing an NHS (N-hydroxysuccinimide) group to PES as described below is allowed to react with the side-chain amino group of a lysine residue introduced in the mutant glucose oxidase. In a preferred method the modification is carried out using a ratio of enzyme to electron acceptor of 1:500 to 1:10,000.

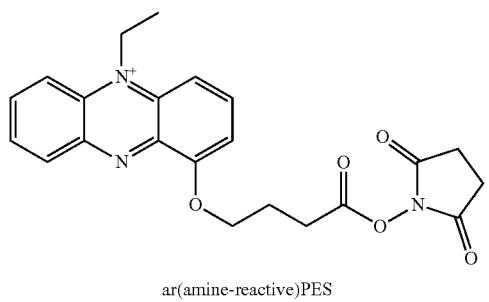 [SMILES: CC[n+]1c2ccccc2nc2c(OCCCC(=O)ON3C(=O)CCC3=O)cccc21]

ar(amine-reactive)PES

1-[3-(Succinimidyloxycarbonyl)propoxy]-5-ethylphenazinium

In cases where a wild-type glucose oxidase intrinsically has an amino acid residue having a reactive functional group in the side chain as the amino acid residue corresponding to the isoleucine at position 489 or the arginine at position 335 in the amino acid sequence of SEQ ID NO:1, the wild-type glucose oxidase can be modified with the electron acceptor even without the introduction of a mutation.

<Biosensor>

By binding the electron acceptor-modified glucose oxidase to an electrode base material, an enzyme electrode of the direct electron transfer type can be obtained, and such an enzyme electrode can be used as a constituent of a biosensor such as a glucose sensor. Examples of an electrode base material include metal electrodes, carbon electrodes, which may be prepared by providing a metal layer or a carbon layer on the surface of an insulating substrate.

The enzyme electrode of the direct electron transfer type herein means an electrode capable of transferring an electron generated by an enzymatic reaction to the electrode without using a free electron acceptor.

The enzyme electrode to which the electron acceptor-modified glucose oxidase is bound can be prepared by a known method. For example, the enzyme electrode can be prepared as follows.

First, a metal layer which functions as an electrode is formed on one side of an insulating substrate. For example, a metal layer having a desired thickness (for example, about 30 nm) is formed by depositing a metallic material, by physical vapor deposition (PVD, for example, sputtering) or chemical vapor deposition (CVD), on one side of an insulating substrate in the form of a film having a predetermined thickness (for example, about 100 μm). Instead of the metal layer, an electrode layer made of a carbon material may be formed.

By applying a solution of the electron acceptor-modified glucose oxidase to the surface of the thus obtained electrode layer, and then drying the solution, the electron acceptor-modified glucose oxidase can be bound to the electrode surface.

Alternatively, the electron acceptor-modified glucose oxidase of the present invention may be immobilized on the electrode surface.

The method for the immobilization of the electron acceptor-modified glucose oxidase on the electrode surface is not limited, and examples of the method include a method using a conductive polymer or a cross-linking agent, and a method using a monolayer-forming molecule.

For example, in cases where a monolayer-forming molecule is used, the monolayer-forming molecule is first bound onto the electrode as disclosed in JP 2017-211383 A. Thereafter, by reacting a reactive functional group of the monolayer-forming molecule with an amino group, carboxyl group, or the like of the glucose oxidase, the glucose oxidase can be immobilized on the electrode through the monolayer-forming molecule.

In cases where the enzyme is immobilized on the electrode using a conductive polymer or a cross-linking agent, the enzyme electrode can be prepared by adding the glucose oxidase and the reagent such as a conductive polymer or a cross-linking reagent onto the electrode as described in, for example, WO 2014/002999 or JP 2016-121989 A.

Examples of the glucose sensor include a glucose sensor which uses, as a working electrode, the above-described enzyme electrode in which the electron acceptor-modified glucose oxidase is bound to the electrode surface. The sensor means a measurement system for electrochemically measuring the concentration of a test substance of interest, and usually contains the following three electrodes: a working electrode (enzyme electrode), a counter electrode (platinum or the like), and a reference electrode (Ag/AgCl or the like). Alternatively, the sensor may be a two-electrode system constituted by a working electrode and a counter electrode, such as the ones used in conventional, simple blood glucose level systems. The sensor preferably further contains a constant-temperature cell in which a buffer and a test sample are to be placed; a power source for applying a voltage to the working electrode; an ammeter; a recorder; and/or the like. The sensor may be either a batch-type sensor or a flow-type sensor. The flow-type sensor may be a sensor capable of continuous measurement of the blood glucose level. More specifically, the sensor may be one having a two-electrode system or a three-electrode system in which the electron acceptor-modified glucose oxidase is immobilized, which electrode system is inserted into a blood sample or a dialysis sample that is continuously supplied, or into blood or interstitial fluid, to perform the measurement. The structure of such an enzyme sensor is well known in the art, and described in, for example, Biosensors-Fundamental and Applications-Anthony P. F. Turner, Isao Karube, and Geroge S. Wilson, Oxford University Press 1987.

The measurement of the glucose level can be carried out as follows. A buffer is placed in the constant-temperature cell of the sensor, and the temperature of is kept constant. As a working electrode, an enzyme electrode to which the electron acceptor-modified glucose oxidase is bound is used. As a counter electrode, for example, a platinum electrode is used. As a reference electrode, for example, an Ag/AgCl electrode is used. A constant voltage is applied to the working electrode. After the electric current becomes constant, a sample containing glucose is placed in the constant-temperature cell, and an increase in the electric current is measured. According to a calibration curve prepared using glucose solutions having standard concentrations, the glucose concentration in the sample can be calculated.

The electron acceptor-modified glucose oxidase can also be used as a constituent of a glucose assay kit. The glucose assay kit may contain, in addition to the electron acceptor-modified glucose oxidase, a coloring or luminescence reagent, a dilution buffer, a standard substance, manufacturer's instructions, and/or the like.

EXAMPLES

The present invention is described below more concretely by way of Examples. However, the present invention is not limited to the Examples.

[Introduction of Mutation]

An artificially synthesized wild-type *Aspergillus niger* 1CF3 structural gene was inserted into the pET30c vector to construct pET30c 1CF3 WT, which is a wild-type 1CF3 expression vector. Using this vector as a template, site-directed mutagenesis was carried out such that the isoleucine at position 489 was substituted with lysine. More specifically, using a commercially available site-directed mutagenesis kit (QuikChange II Site-Directed Mutagenesis Kit, Stratagene), codon modification of the 1CF3 structural gene contained in the pET30c 1CF3 WT was carried out such that the isoleucine at position 489 was substituted with lysine.

*E. coli* BL21 (DE3) was transformed with the thus constructed pET30c 1CF3 I489K or pET30c 1CF3 WT, to obtain a mutant 1CF3- or wild-type 1CF3-expressing *E. coli*.

[Method for Preparing Mutant Enzyme]

1. *E. coli* BL21 (DE3)/pET30c 1CF3 WT, I489K was precultured in 3 mL of LB medium (with kanamycin at a final concentration of 50 μg/mL) at 37° C. for 12 hours under aerobic conditions. After inoculation of the precultured cells to 100 mL of the same medium, IPTG induction (final concentration, 0.5 mM) was carried out when the OD660 reached 0.6, and then shake culture was carried out at 20° C. for 24 hours. After collecting the cells, the wet cells were resuspended in 20 mM P. P. B (pH 7.0), and then sonicated, followed by performing centrifugation (10,000 g, 4° C., 20 min) to obtain a water-soluble fraction and an insoluble fraction.

2. The insoluble fraction was suspended in 1 mL of washing buffer 1 (100 mM NaCl, 1 mM EDTA, 1% Triton X; 20 mM Tris-HCl (pH8.0)), and then incubated at 1500 rpm at 4° C. for 1 hour, followed by performing centrifugation (10,000 g, 4° C., 10 min).

3. The same operation was then carried out for the insoluble fraction obtained, using washing buffer 2 (100 mM NaCl, 1 mM EDTA; 20 mM Tris-HCl (pH8.0)) and washing buffer 3 (2 M urea; 20 mM Tris-HCl (pH 8.0)).

4. The sample was suspended in 0.75 mL of solubilization buffer (8 M urea, 30 mM dithiothreitol; 20 mM Tris-HCl), and then incubated at 1500 rpm at 4° C. for 4 hours, followed by performing centrifugation (10,000 g, 4° C., 10 min). The solubilized inclusion body fraction obtained was diluted with refolding buffer (1 mM reduced glutathione, 1 mM oxidized glutathione, flavin adenine dinucleotide, 10% glycerol; 20 mM P. P. B (pH 7.5)) to a final concentration of 0.05 mg/mL, and the resulting dilution was left to stand at 10° C. for 96 hours.

5. The sample was concentrated (about 100-fold concentration) by ultrafiltration using Amicon Ultra 30 K (Merk Millipore). The concentrated sample was subjected to dialysis against 20 mM sodium acetate (pH 5.0) for 12 hours, and then against 20 mM P. P. B (pH 7.0) for 24 hours, followed by performing centrifugation (20,000 g, 4° C., 5 min) to obtain the supernatant as a purified enzyme.

[Chemical Modification with Electron Acceptor]

For arPES modification, four kinds of reaction solutions with molar ratios, between the purified enzyme (mutant I489K or wild type WT) and arPES, of 1:500, 1:1000, 1:5000, and 1:10000 were prepared using 50 mM Tricine (pH 8.3) as a buffer, and the reaction solutions were shaken at 1200 rpm at 25° C. for 2 hours. For buffer replacement, each sample was subjected to ultrafiltration (14,000 g, 4° C., 5 min) using Amicon Ultra 30 K, and the concentrated sample was diluted with 20 mM P. P. B. This operation was repeated 10 times. The mutant type is modified with PES through position 489 and natural side-chain amino groups at other positions, and the wild type is modified with PES through natural side-chain amino groups.

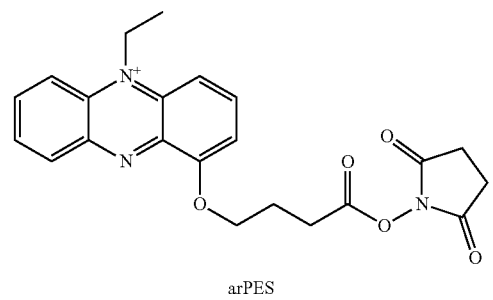 [SMILES: CC[n+]1c2ccccc2nc2c(OCCCC(=O)ON3C(=O)CCC3=O)cccc21]

arPES

[Measurement of Enzymatic Activity]

Evaluation of the enzymatic activity was carried out for the modified enzyme and the unmodified enzyme, in the presence or absence of PMS.

Reduction reaction of MTT with arPES or PMS was measured by monitoring changes in the absorbance at 565 nm over time. The reaction conditions were as follows unless otherwise specified.

The reaction was started by adding a substrate to a reaction solution (200 μL; 20 mM PPB (pH 7.0)+1.0 mM MTT; all concentrations are expressed as final concentrations) containing the enzyme solution, and changes in the absorbance at 565 nm were measured (in the cases where PMS was added, its final concentration was set to 0.6 mM).

As a substrate, glucose at a final concentration of 100 mM was used. The amount of the enzyme with which reduction of 1 μmol of MTT was achieved was defined as 1 unit, and the activity value was calculated according to the following equation. The molar absorption coefficient of MTT at pH 7.0 was defined as 20 mM$^{-1}$ cm$^{-1}$.

$$\text{Unit/ml} = \angle \text{ABS/min} \times 1/20^{*1} \times 40^{*2}$$

*1: The molar absorption coefficient of MTT at pH 7.0
*2: The dilution factor of the enzyme solution in the reaction solution The results are shown in Table 4.

In the wild-type sample after the modification, no dehydrogenase activity in the MTT system was observed. It was thus found that the wild type did not allow electron transfer by the arPES after the modification. In contrast, regarding the mutant after the PES-modification, all samples with the various concentration ratios showed activity in the MTT system, indicating electron transfer by arPES after the modification. The optimum concentration ratio for the modification was shown to be 1:1000, at which the highest activity was achieved. It was thus suggested that the electron transfer in glucose oxidase was caused by the arPES with which the lysine residue introduced by the substitution at position 489 was modified.

TABLE 4

Activity of PES-modified GOX (I489K or wild type)

| | Dh (U/mg) | | | |
| --- | --- | --- | --- | --- |
| | I489K | | WT | |
| Enzyme:arPES | MTT | PMS/MTT | MTT | PMS/MTT |
| 1:500 | 3.4 | 44 | $2.4 \times 10^{-1}$ | 35 |
| 1:1000 | 22 | 66 | not detected | 47 |
| 1:5000 | 15 | 45 | $2.0 \times 10^{-1}$ | 27 |
| 1:10000 | 12 | 36 | net detected | 21 |
| NOT modified | not detected | 14 | $2.1 \times 10^{-1}$ | 21 |

Substrate glucose 100 mM
Dh: dehydrogenase activity

[Preparation of Sensor and Measurement of Glucose Concentration]

1. An enzyme ink (0.78 mg/ml GOX, 0.4% KJB stock (conductive carbon black, Lion Specialty Chemicals), 3% Epocros (oxazoline group-containing water-soluble polymer, Nippon Shokubai), 0.5% trehalose) was prepared.

As the enzyme, wild-type GOX (1CF3WT), mutant GOX (1CFI489K), arPES-modified wild-type GOX (arPES-WT), or arPES-modified mutant GOX (arPES-I489K) was used.

2. On a carbon-printed electrode, 160 nL of the above mixed ink was spotted and dried, followed by heat treatment at 100° C. for 2 h.

3. Using a sensor of a three-electrode system (WE: SPCE/enzyme ink, CE: carbon-printed, RE: Ag/AgCl), amperometric measurement was carried out at 0 mV vs. Ag/AgCl at 25° C. for Glu 0, 50, 100, 300, or 600 mg/dL.

Figure 2:
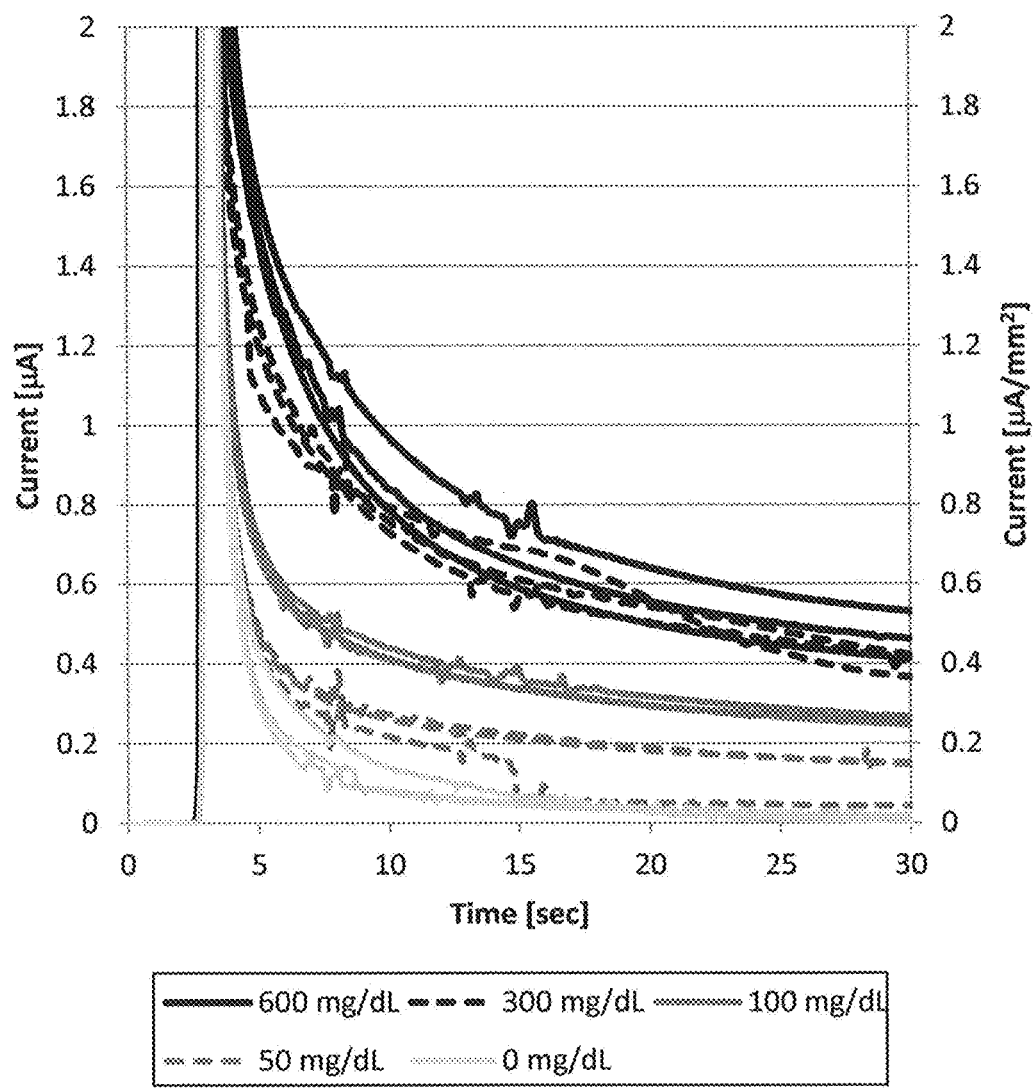
FIG. 2 shows a graph showing results of amperometric measurement using a sensor including a PES-modified enzyme obtained by modifying I489K mutant-type GOX with PES.
Figure 3:
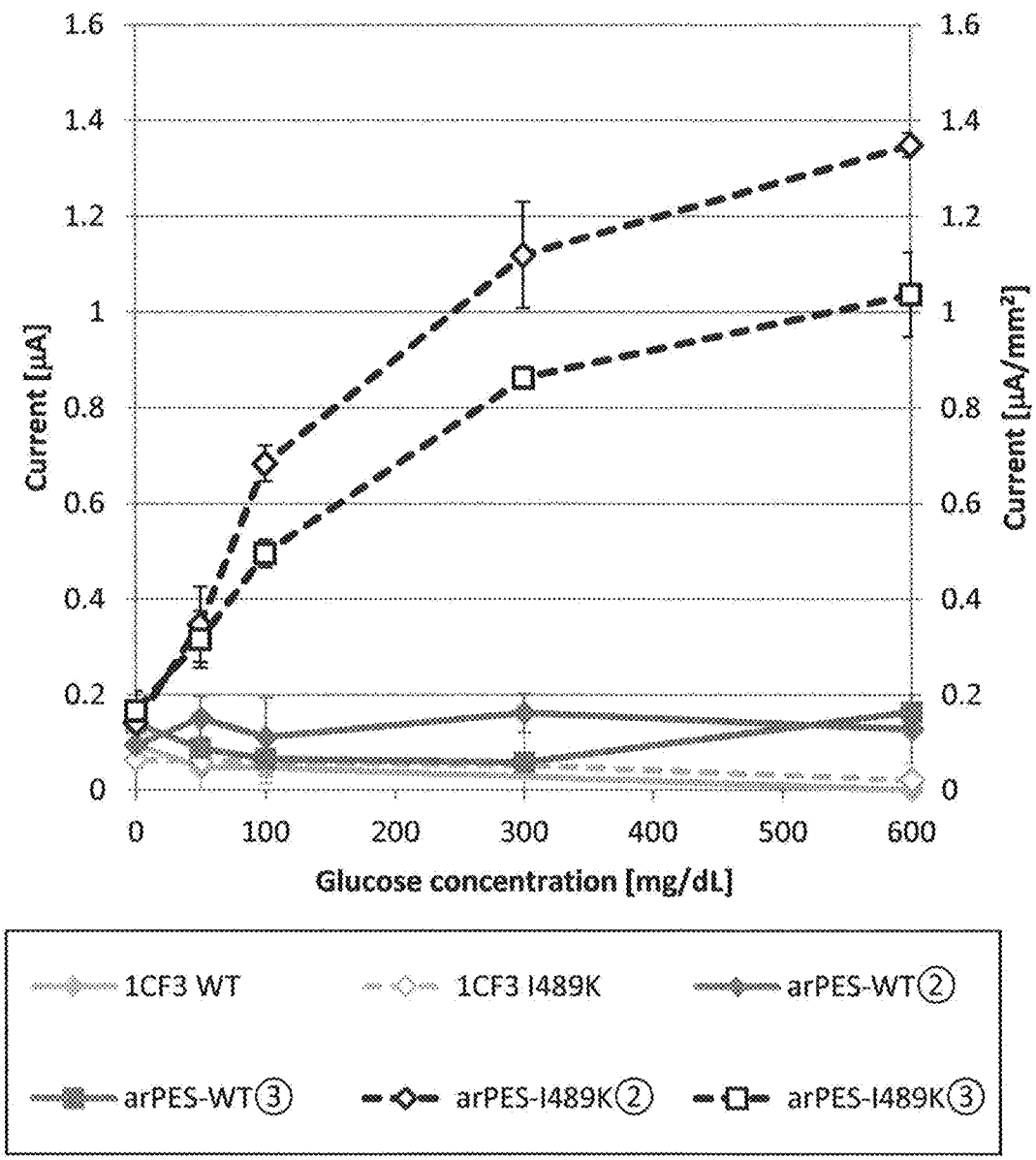
FIG. 3 shows a graph showing the relationship between the glucose concentration and the current value for wild-type and mutant GOX enzymes and PES-modified versions of those enzymes.

The results are shown in FIGS. 1 to 3.

As shown in FIG. 1, with the sensor having an electrode in which the wild-type 1CF3 was modified with PES (arPES-WT), no electric current dependent on the glucose concentration could be detected. In contrast, as shown in FIG. 2, with the sensor having an electrode in which the mutant 1CF3 was modified with PES (arPES-I489K), electric currents dependent on the glucose concentration could be detected. FIG. 3 shows the relationship between glucose concentration and current value for the various modified and unmodified wild-type and mutant GOX that were tested.

While the invention has been described in detail with reference to exemplary embodiments thereof, it will be apparent to one skilled in the art that various changes may be made, and equivalents employed, without departing from the scope of the invention. Each of the aforementioned documents as well as JP2018-098011 is incorporated by reference herein in its entirety.

What is claimed is:

1. A mutant glucose oxidase comprising an amino acid sequence in which a residue corresponding to isoleucine at position 489 or arginine at position 335 in the amino acid sequence of SEQ ID NO:1 is substituted with an amino acid residue having a reactive functional group in a side chain, wherein said mutant glucose oxidase is selected from the group consisting of:
 a) mutant glucose oxidase comprising an amino acid sequence with a sequence identity of not less than 90% to the amino acid sequence of SEQ ID NO: 2 wherein said residue corresponding to isoleucine at position 489 in the amino acid sequence of SEQ ID NO: 1 is valine at position 511 in the amino acid sequence of SEQ ID NO: 2 and said residue corresponding to arginine at position 335 in the amino acid sequence of SEQ ID NO: 1 is arginine at position 357 in the amino acid sequence of SEQ ID NO: 2,
 b) mutant glucose oxidase comprising an amino acid sequence with a sequence identity of not less than 90% to the amino acid sequence of SEQ ID NO: 3 wherein said residue corresponding to isoleucine at position 489 in the amino acid sequence of SEQ ID NO: 1 is threonine at position 517 in the amino acid sequence of SEQ ID NO: 3 and said residue corresponding to arginine at position 335 in the amino acid sequence of SEQ ID NO: 1 is alanine at position 363 in the amino acid sequence of SEQ ID NO: 3,
 c) mutant glucose oxidase comprising an amino acid sequence with a sequence identity of not less than 90% to the amino acid sequence of SEQ ID NO: 4 wherein said residue corresponding to isoleucine at position 489 in the amino acid sequence of SEQ ID NO: 1 is isoleucine at position 512 in the amino acid sequence of SEQ ID NO: 4 and said residue corresponding to arginine at position 335 in the amino acid sequence of SEQ ID NO: 1 is arginine at position 358 in the amino acid sequence of SEQ ID NO: 4,
 d) mutant glucose oxidase comprising an amino acid sequence with a sequence identity of not less than 90% to the amino acid sequence of SEQ ID NO: 5 wherein said residue corresponding to isoleucine at position 489 in the amino acid sequence of SEQ ID NO: 1 is leucine at position 493 in the amino acid sequence of SEQ ID NO: 5 and said residue corresponding to arginine at position 335 in the amino acid sequence of SEQ ID NO: 1 is serine at position 339 in the amino acid sequence of SEQ ID NO: 5,
 e) mutant glucose oxidase comprising an amino acid sequence with a sequence identity of not less than 90% to the amino acid sequence of SEQ ID NO: 6 wherein said residue corresponding to isoleucine at position 489 in the amino acid sequence of SEQ ID NO: 1 is isoleucine at position 512 in the amino acid sequence of SEQ ID NO: 6 and said residue corresponding to arginine at position 335 in the amino acid sequence of SEQ ID NO: 1 is arginine at position 358 in the amino acid sequence of SEQ ID NO: 6, f) mutant glucose oxidase comprising an amino acid sequence with a sequence identity of not less than 90% to the amino acid sequence of SEQ ID NO: 7 wherein said residue corresponding to isoleucine at position 489 in the amino acid sequence of SEQ ID NO: 1 is isoleucine at position 509 in the amino acid sequence of SEQ ID NO: 7 and said residue corresponding to arginine at position 335 in the amino acid sequence of SEQ ID NO: 1 is arginine at position 355 in the amino acid sequence of SEQ ID NO: 7, and g) mutant glucose oxidase comprising an amino acid sequence with a sequence identity of not less than 90% to the amino acid sequence of SEQ ID NO: 8 wherein said residue corresponding to isoleucine at position 489 in the amino acid sequence of SEQ ID NO: 1 is isoleucine at position 510 in the amino acid sequence of SEQ ID NO: 8 and said residue corresponding to arginine at position 335 in the amino acid sequence of SEQ ID NO: 1 is arginine at position 357 in the amino acid sequence of SEQ ID NO: 8.

2. The mutant glucose oxidase according to claim 1, wherein the amino acid residue having a reactive functional group in the side chain is a lysine residue.

3. An electron acceptor-modified glucose oxidase obtained or obtainable by introducing an electron acceptor to the mutant glucose oxidase according to claim 1, wherein the electron acceptor has been introduced to the glucose oxidase through the amino acid residue having a reactive functional group in the side chain.

4. The electron acceptor-modified glucose oxidase according to claim 3, wherein the electron acceptor is a phenazinium compound.

5. The electron acceptor-modified glucose oxidase according to claim 4, wherein the phenazinium compound is represented by the following formula:

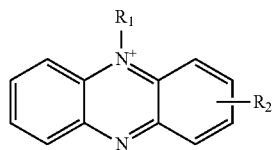

wherein R1 represents a hydrocarbyl group, and R2 represents a linker.

6. An enzyme electrode comprising an electrode base material and the electron acceptor-modified glucose oxidase according to claim 3 bound to the base material.

7. A biosensor comprising the enzyme electrode according to claim 6.

8. The mutant glucose oxidase according to claim 1, wherein said mutant glucose oxidase has an amino acid sequence with a sequence identity of not less than 90% to the amino acid sequence of SEQ ID NO: 2.

9. The mutant glucose oxidase according to claim 1, wherein said mutant glucose oxidase has an amino acid sequence with a sequence identity of not less than 90% to the amino acid sequence of SEQ ID NO: 3.

10. The mutant glucose oxidase according to claim 1, wherein said mutant glucose oxidase has an amino acid sequence with a sequence identity of not less than 90% to the amino acid sequence of SEQ ID NO: 4.

11. The mutant glucose oxidase according to claim 1, wherein said mutant glucose oxidase has an amino acid sequence with a sequence identity of not less than 90% to the amino acid sequence of SEQ ID NO: 5.

12. The mutant glucose oxidase according to claim 1, wherein said mutant glucose oxidase has an amino acid sequence with a sequence identity of not less than 90% to the amino acid sequence of SEQ ID NO: 6.

13. The mutant glucose oxidase according to claim 1, wherein said mutant glucose oxidase has an amino acid sequence with a sequence identity of not less than 90% to the amino acid sequence of SEQ ID NO: 7.

14. The mutant glucose oxidase according to claim 1, wherein said mutant glucose oxidase has an amino acid sequence with a sequence identity of not less than 90% to the amino acid sequence of SEQ ID NO: 8.

15. The mutant glucose oxidase according to claim 1, wherein said mutant glucose oxidase has an amino acid sequence with a sequence identity of not less than 95% to the amino acid sequence of SEQ ID NO: 2.

16. The mutant glucose oxidase according to claim 1, wherein said mutant glucose oxidase has an amino acid sequence with a sequence identity of not less than 98% to the amino acid sequence of SEQ ID NO: 2.

* * * * *